United States Patent [19]

Hamazaki

[11] Patent Number: 5,679,110
[45] Date of Patent: Oct. 21, 1997

[54] ENDOSCOPE COVER ATTACHING APPARATUS

[75] Inventor: Masanori Hamazaki, Hachioji, Japan

[73] Assignee: Olympus Optical Co., Ltd., Tokyo, Japan

[21] Appl. No.: 395,304

[22] Filed: Feb. 28, 1995

[30] Foreign Application Priority Data

May 26, 1994 [JP] Japan .................. 6-113083

[51] Int. Cl.⁶ ........................................ A61B 1/04
[52] U.S. Cl. .................. 600/124; 600/121; 600/122; 600/102
[58] Field of Search .................. 600/121, 122, 600/123, 124, 102; 312/209; 248/121, 122; 269/329, 902, 909; 604/163, 171, 192

[56] References Cited

U.S. PATENT DOCUMENTS

| | | | |
|---|---|---|---|
| 4,854,301 | 8/1989 | Nakajima | 600/102 |
| 4,907,395 | 3/1990 | Opie et al. | 52/434 |
| 5,337,731 | 8/1994 | Takahashi et al. | 600/121 X |

Primary Examiner—Richard J. Apley
Assistant Examiner—Beverly M. Flanagan
Attorney, Agent, or Firm—Armstrong, Westerman Hattori, McLeland & Naughton

[57] ABSTRACT

There is disclosed an endoscope cover attaching apparatus including: a cover holding stage for holding an endoscope cover in the form of a straight line, the endoscope cover including an insertion part cover for covering the insertion part of an endoscope, and an insertion part inlet aperture located at an end of said insertion part cover near a hand operation position, wherein a tube is disposed in said endoscope cover; an operation part holding stage for holding the operation part of the endoscope, the endoscope including the insertion part in which an observation optical system is disposed, and the operation part which also serves as a grip of the endoscope; and rotation means for adjusting the rotational position of the operation part of the endoscope relative to the rotational position of the insertion part inlet aperture of the endoscope cover, wherein the rotation means is disposed at least either on the operation part holding stage or on the cover holding stage.

42 Claims, 26 Drawing Sheets

FIG.3
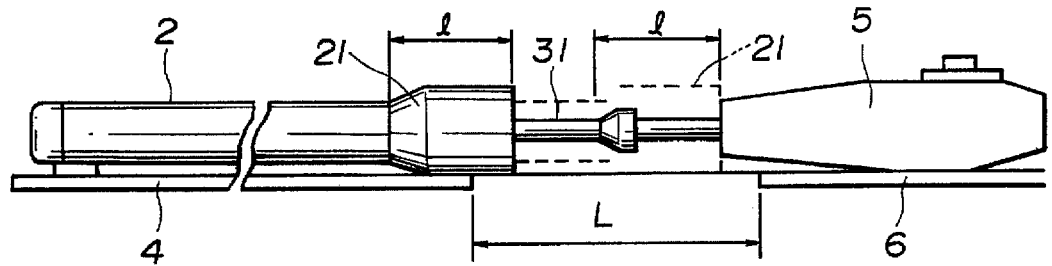
FIG.4A             FIG.4B
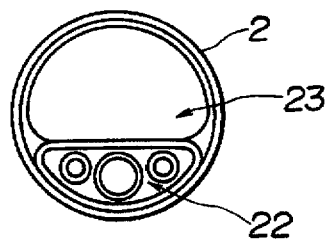   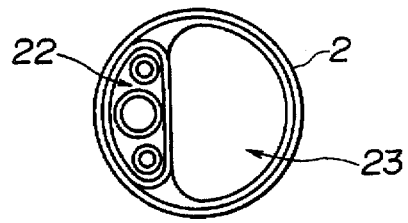
FIG.5
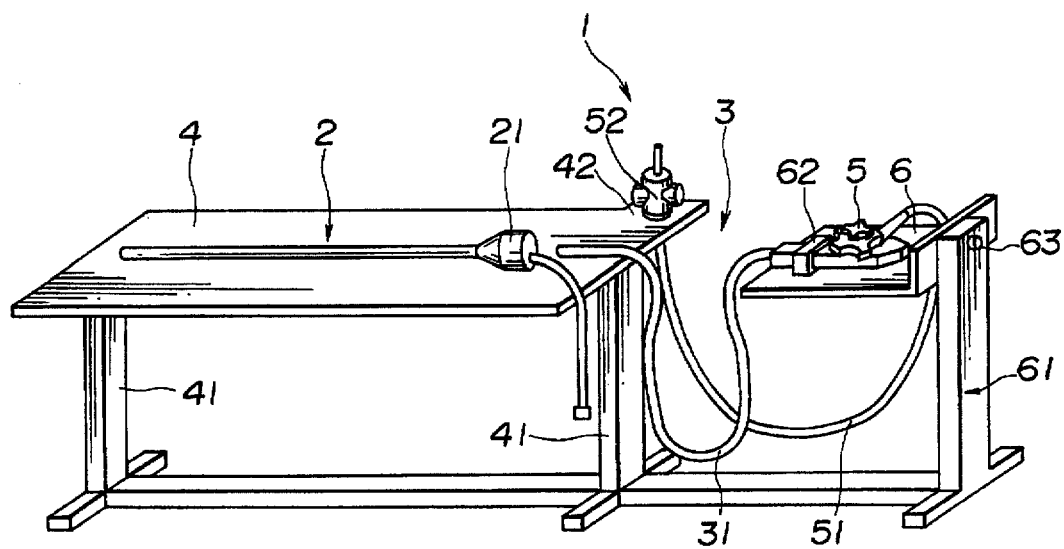

ENDOSCOPE COVER ATTACHING APPARATUS

BACKGROUND OF THE INVENTION

1. Field of the Invention

The present invention relates to an endoscope cover attaching apparatus for attaching an endoscope cover to an endoscope.

2. Related Art Statement

Before using again an endoscope that has been used once for a medical examination or treatment, the endoscope is subjected to cleaning or disinfection so as to prevent infection via the endoscope. However, reliable cleaning or disinfection of a used endoscope needs rather a long time. Therefore, the cleaning and disinfection procedure result in a reduction in efficiency in use of the endoscope. One known technique to improve the efficiency in use of the endoscope is to cover an endoscope itself with a cover element. A medical examination or treatment is performed using the endoscope with the cover. After the completion of the medical examination or treatment, only the cover is disposed of Thus, the endoscope itself is maintained clean. This technique is referred to as a covered-type endoscope.

The covered-type endoscope comprises an endoscope and an endoscope cover that is attached to the endoscope. Before performing a medical examination or treatment, an endoscope that has been disinfected in advance is covered with an endoscope cover that has also been disinfected already. Then, the endoscope covered with the endoscope cover is inserted into a body cavity of a patient thereby performing a medical examination or treatment.

After the completion of the examination or the treatment, the endoscope cover is removed from the endoscope and only the endoscope cover is disposed of. After the removal of the endoscope cover, a new disinfected endoscope cover is attached to the endoscope for reuse. This technique allows an endoscope to be used continuously without having to be cleaned for each medical examination or treatment. Thus, the endoscope can be used in a more efficient manner. In the case of an endoscope of the type that is inserted into a body cavity via a mouth cavity, the endoscope has a long, thin, and flexible insertion part. However, this structure makes it difficult to attach an endoscope cover to the endoscope. To make it easier to attach an endoscope cover to an endoscope, various types of endoscope cover attaching apparatus have been proposed. For example, Japanese Patent Laid-Open No. H-5-49592 discloses an endoscope stand for use in attaching an endoscope cover to an endoscope to be covered. Japanese Patent Laid-Open No. H-4-357920 discloses a technique in which an endoscope cover is expanded by supplying air into the endoscope cover thereby increasing the clearance between the endoscope cover and the insertion part of an endoscope to be covered and thus making it easier to perform attachment.

In general, in addition to an endoscope itself, tubes for supplying air and water are disposed in an endoscope cover forming a covered-type endoscope. This is achieved by employing a structure in which the insertion part of an endoscope to be covered is formed such that it has a D-shaped or semi-circular-shaped cross section and the inside of an endoscope cover is divided into two spaces: one is an endoscope space for accepting an endoscope to be covered, and the other is a tube space in which tubes such as an air tube, water tube, etc., are disposed.

However, this technique has a disadvantage that when the insertion part of an endoscope, shaped in a long, thin, and flexible form, is inserted into an endoscope cover, the insertion part of the endoscope often gets entangled with the tubes disposed inside the endoscope cover. One known technique to prevent the insertion part of an endoscope from petting entangled with the tubes disposed inside an endoscope cover is to place the endoscope cover in such a manner that the tubes in the endoscope cover come to the lowest possible position so that the insertion part of the endoscope does not get with the tubes. The relative position between tubes disposed in an endoscope cover and an endoscope placed in the endoscope cover varies depending on the type of the endoscope. However, in the above-described endoscope stand disclosed in Japanese Patent Laid-Open No. H-5-49592, the operation part of an endoscope to be covered is held at a fixed position. As a result, in some types of endoscope, tubes in an endoscope cover can come to an upper position. Therefore, this technique still has a problem that there is a possibility that the insertion part of an endoscope gets entangled with tubes in an endoscope cover during an attaching operation of inserting the insertion part of the endoscope into the endoscope cover.

OBJECTS AND SUMMARY OF THE INVENTION

It is an object of the present invention to provide an endoscope cover attaching apparatus capable of smoothly attaching an endoscope cover to an endoscope without such a problem that the insertion part of the endoscope gets entangled with a tube of the endoscope cover.

It is another object of the present invention to provide an endoscope cover attaching apparatus that can be used not only to attach an endoscope cover to an endoscope but also to remove an endoscope cover from an endoscope.

According to an aspect of the present invention, there is provided an endoscope cover attaching apparatus including: a cover holding stage for holding an endoscope cover in the form of a straight line, the endoscope cover including an insertion part cover for covering the insertion part of an endoscope, and an insertion part inlet aperture located at an end of said insertion part cover near a hand operation position, wherein a tube is disposed in said endoscope cover; an operation part holding stage for holding the operation part of the endoscope, the endoscope including the insertion part in which an observation optical system is disposed, and the operation part which also serves as a grip of the endoscope; and rotation means for adjusting the rotational position of the operation part of said endoscope relative to the rotational position of the insertion part inlet aperture of said endoscope cover, wherein said rotation means is disposed at least either on said operation part holding stage or on said cover holding stage.

According to another aspect of the present invention, there is provided an endoscope cover attaching apparatus, including: an operation part holding stage having means for holding the operation part of an endoscope at a variable angle between the longitudinal axis of the operation part and the vertical direction, the endoscope including an insertion part in which an observation optical system is disposed, and the operation part which also serves as a grip of the endoscope; and a cover holding stage having means for holding an endoscope cover at a variable angle between the longitudinal axis of the endoscope cover and the vertical direction, the endoscope cover including an insertion part cover for covering the insertion part of the endoscope, and an insertion part inlet aperture located at an end of said insertion part cover near a hand operation position, wherein a tube is disposed in said endoscope cover.

These and other features and advantages of the invention will be more apparent from the following detailed description of the invention.

BRIEF DESCRIPTION OF THE DRAWINGS

FIGS. 1 to 5 relate to a first embodiment of the present invention, wherein:

FIG. 1 is a schematic diagram illustrating an endoscope cover attaching apparatus;

FIG. 2 is a schematic diagram illustrating rotation means of an operation part holding stage; wherein:

FIG. 3 is a schematic diagram illustrating a relationship between the length of an inlet portion and the space between the operation part holding stage and the cover holding stage;

FIG. 4 is a schematic diagram illustrating rotational positions of an endoscope cover placed on the cover holding stage, wherein:

FIG. 4A illustrates an endoscope cover placed such that tubes are at the lowest possible position; and FIG. 4B illustrates an endoscope cover placed such that tubes are parallel to the vertical direction;

FIG. 5 is a schematic diagram illustrating a state in which an endoscope cover is going to be attached to an endoscope.

FIG. 7 and FIG. 8 relate to an endoscope cover attaching apparatus having a modified structure, wherein:

FIG. 7 is a schematic diagram illustrating a general structure of an endoscope cover attaching apparatus; and FIG. 8 is a schematic diagram illustrating various cross-sectional shapes of a cover holding stage, wherein:

FIG. 12 is a schematic diagram illustrating an endoscope cover attaching apparatus capable of automatically attaching an endoscope cover to an endoscope to be covered, wherein:

FIGS. 13 and 14 relate to a third embodiment of the present invention, wherein:

FIG. 13 is a schematic diagram generally illustrating a structure of an endoscope cover attaching apparatus; and FIG. 14 is a schematic diagram illustrating the operation of the endoscope cover attaching apparatus, wherein:

FIG. 15 is a schematic diagram illustrating a fourth embodiment of an endoscope cover attaching apparatus according to the present invention, wherein

FIGS. 16 and 17 relate to a fifth embodiment of the present invention, wherein:

FIG. 16 is a schematic diagram generally illustrating a structure of an endoscope cover attaching apparatus; and FIG. 17 is a schematic diagram illustrating a state in which an endoscope cover has been attached to an endoscope using the endoscope cover attaching apparatus;

FIG. 21 is a schematic diagram illustrating another structure of an arm, wherein

FIG. 22 is a schematic diagram illustrating another structure of an arm, wherein:

FIGS. 23 to 25 relate to a seventh embodiment of the present invention, wherein:

FIG. 23 is a side view illustrating a general structure of an operation part holding stage;

FIG. 24 is a side view illustrating a state in which the insertion part of an endoscope to be covered is being inserted into an endoscope cover; and FIG. 25 is a front view of FIG. 24;

FIG. 28 is a schematic diagram illustrating functions of the cover holding stage, wherein:

FIG. 29 is a schematic diagram illustrating another structure of a cover holding stage, wherein:

FIG. 30 is a schematic diagram illustrating another structure of a first hanger, wherein:

FIGS. 33 to 38 illustrate the endoscope cover attaching apparatus according to the seventh embodiment of the invention, in various situations during a day's use, wherein:

FIG. 33 is a schematic diagram for explanation of a preparatory procedure prior to an examination, wherein:

FIG. 34 is a schematic diagram illustrating a procedure of attaching and removing a cover, wherein:

FIG. 35 is a schematic diagram for explanation of a preparatory procedure prior to an examination;

FIG. 36 is a schematic diagram for explanation of a procedure after an examination, wherein:

FIG. 37 is a schematic diagram for explanation of an procedure of an air tight test after an examination, wherein:

FIG. 38 is a schematic diagram illustrating a procedure at the end of a day, wherein:

FIG. 40 is a schematic diagram illustrating another method of connecting the operation part to the inlet portion, wherein:

FIG. 46 is a schematic diagram illustrating a tube and a connecting portion of a covered-type endoscope, wherein:

DETAILED DESCRIPTION OF THE PREFERRED EMBODIMENTS

Figure 1:
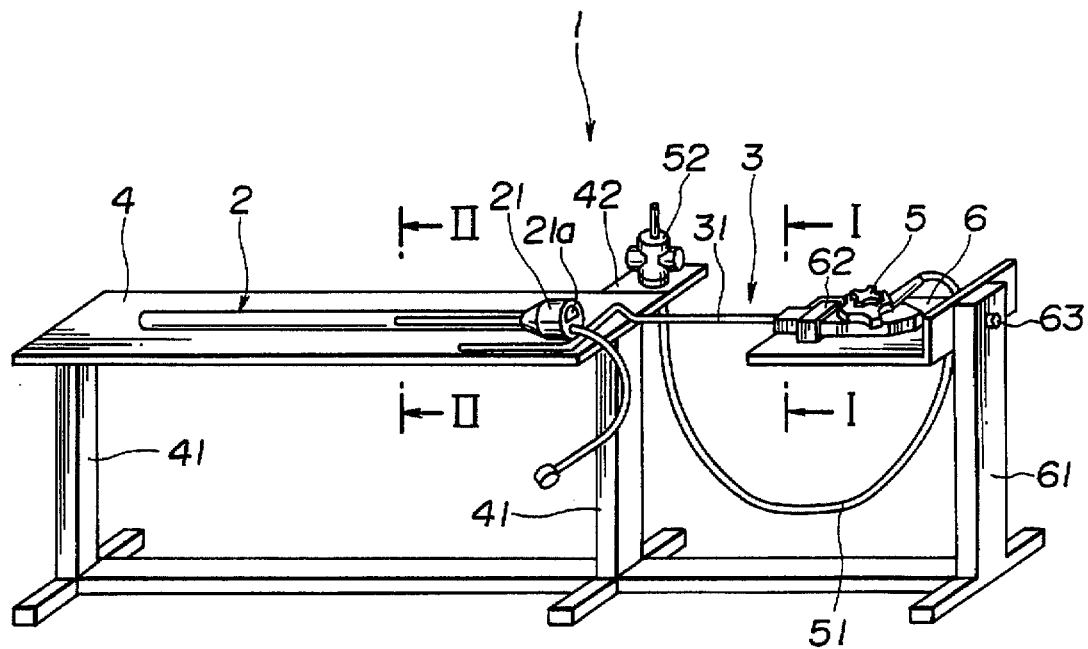

FIGS. 1 to 5 relate to a first embodiment of the present invention, wherein: FIG. 1 is a schematic diagram illustrating an endoscope cover attaching apparatus; FIG. 2 is a schematic diagram illustrating rotation means disposed on an operation part holding stage; FIG. 3 is a schematic diagram illustrating a relationship between the length of an inlet portion and the space between the operation part holding stage and the cover holding stage; FIG. 4 is a schematic diagram illustrating a rotational position of an endoscope cover placed on the cover holding stage; and FIG. 5 is a schematic diagram illustrating a state in which an endoscope cover is going to be attached to an endoscope.

The endoscope cover attaching apparatus (hereinafter referred to as cover attaching apparatus) shown in FIG. 1 is an apparatus for attaching an endoscope cover 2 to an endoscope 3 to be covered. The cover attaching apparatus 1 comprises: a cover holding stage 4 having a length long enough to hold an endoscope cover 2 in the form of a straight line, wherein various tubes such as an air tube, water tube, suction tube are disposed in the endoscope cover 2; and an operation part holding stage 6 for holding an operation part 5 and an operation-part-side portion of the flexible insertion part 31 of an endoscope 3 in the same direction as that in which the endoscope cover is placed, wherein the operation part 5 also serves as a grip and wherein the insertion part 31 has a D-like cross section and extends from the endoscope 3 to be covered.

The cover holding stage 4 is held by two legs 41, 41 and the operation part holding stage 6 is held by a post 61 which is in turn held by one of the legs 41 such that these elements form a cover attaching apparatus 1 in an integral form. An endoscope cover 2 is placed in the form of a straight line on the cover holding stage 4 in such a manner that the inlet aperture 21a formed in the inlet portion 21 of the endoscope cover 2 faces the operation part holding stage, and the tubes are at the lowest possible position.

The operation part holding stage 6 has an operation part fixing mechanism 62 for fixing the operation part 5 of an endoscope 3 to be covered in such a manner that the operation part 5 is substantially parallel to the operation part holding stage 6. Furthermore, as shown in FIG. 2, the operation part holding stage 6 is supported by the post 61 via a fixing pin 63 acting as rotation means for rotating the operation part held on the operation part holding stage 6 relative to the inlet portion 21 of the endoscope cover 2. In this state, the center axis 5a of the operation part 5, the rotation axis of the fixing pin 63, and the center axis 2a of the endoscope cover all substantially lie on the same line. Therefore, in the case where there is inconsistency in rotational position of end faces facing each other between the inlet aperture of the endoscope cover 2 held on the cover holding stage 4 and the operation part 5 held on the operation part holding stage 6, it is possible to correct the inconsistency by rotating the operation part holding stage 6 using the rotation means until the rotational position of the inlet aperture of the endoscope cover comes to a position substantially consistent with the rotational position of the operation part of the endoscope.

A universal cord 51 extends from a side portion of the operation part 5 of the endoscope 3 to be covered, and the universal cord 51 has a connector 52 at the other end. The connector 52 is held by a connector holder 42 disposed at a side of the cover holding stage 4 near the operation part holding stage as shown in FIG. 1.

Furthermore, as shown in FIG. 3, the space L between the cover holding stage 4 and the operation part holding stage 6 is set such that l<L wherein l denotes the length of the inlet portion 21 of the endoscope cover 2.

The cover attaching apparatus 1 arranged in the above-described manner functions as follows.

First, a disinfected endoscope cover 2 is placed on the cover holding stage 4 in such a manner that the tube portion 22 provided in the endoscope cover 2 is at the lowest possible position as shown in FIG. 4A.

Figure 2A:
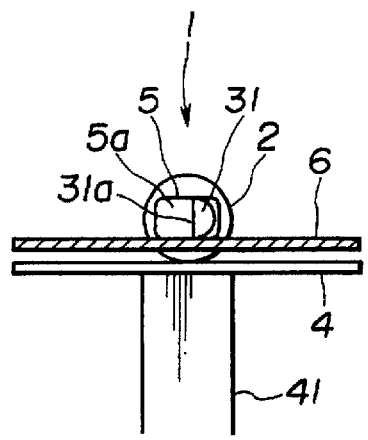
FIG. 2A is a schematic diagram illustrating a positional relationship between an endoscope cover and the operation part of an endoscope in an initial state.

The operation part 5 of the endoscope 3 to be covered is then fixed to the operation part holding stage 6 with the fixing mechanism 62. At this stage, as shown in FIG. 1, the operation part 5 of the endoscope 3 to be covered, that is fixed to the operation part holding stage 6 with the operation part fixing mechanism 62, and the operation-part-side portion of the insertion part 31 of the endoscope, wherein the insertion part 31 has a D-shaped cross section and extends from the operation part 5, are opposite to the inlet aperture of the endoscope cover held on the cover holding stage 4 and lie on the same straight line. However, as shown in FIG. 2A, there is inconsistency in rotational position of end faces facing each other between the insertion part, having a D-shaped cross section, of the endoscope 3 to be covered and the inlet aperture formed in the inlet portion 21 of the endoscope cover 2. Therefore, if, under this condition, the insertion part 31 of the endoscope 3 to be covered is inserted into the endoscope cover, there is a possibility that the insertion part gets entangled with the tube portion 22. Furthermore, if it is tried to force the inlet aperture 23 to face the fixed insertion part 31 of the endoscope 3 to be covered, the tube portion 22 provided in the endoscope cover 2 may come to the vertical position, and thus the insertion part 31 may get entangled with the tube portion 22. At this stage, the insertion part 31 of the endoscope 3 to be covered is placed on the cover holding stage 4 along the endoscope cover.

Figure 2B:
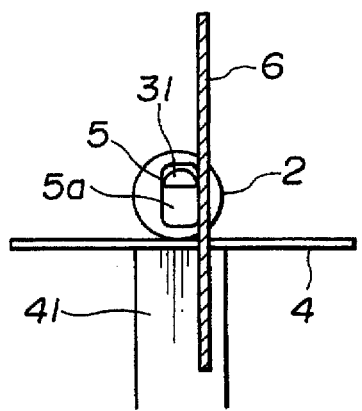
FIG. 2B is a schematic diagram illustrating a state in which the operation part holding stage has been rotated so that the operation part has come to a position that matches the position of the endoscope cover.

In this case, the fixing pin 63 fixing the operation part holding stage 6 of the cover attaching apparatus 1 is unfastened, and the operation part holding stage 6 is rotated about 90° in the counter-clockwise direction. Thus, the operation part 5 held by the operation part fixing mechanism 62 of the operation part holding stage 6 rotates about the fixing pin 63, and the D-shaped insertion part 31 comes to the correct rotational position consistent with the rotational position of the inlet aperture 21a formed in the inlet portion 21 of the endoscope cover 2, as shown in FIG. 2B.

Under this condition in which the insertion part 31 having the D-shaped cross section is at the correct rotational position consistent with the rotational position of the inlet aperture 21, the end portion of the insertion part 31 of the endoscope 3 to be covered is held by a hand and the insertion part 31 of the endoscope 3 is inserted into the endoscope cover. In this situation, as shown in FIG. 5, the middle portion of the insertion part 31 dangles downward between the cover holding stage 4 and the operation part holding stage 6 in such a manner that the dangling portion of the insertion part 31 has no contact to a floor. After the insertion part 31 has been inserted into the endoscope cover until it has reached the deepest position as shown by broken lines, the operation part 5 is fitted and fixed to the inlet portion 21 into one piece. Thus, the attachment of the endoscope cover to the endoscope is complete. As described above, the operation part holding stage of the cover attaching apparatus has the rotation means for rotating the operation part of the endoscope held on the operation pert holding stage around the center axis of the endoscope cover. In operation, thus, the operation part of the endoscope to be covered is fixed to the operation part holding stage with the fixing mechanism and the operation part holding stage is rotated so as to adjust the rotational position of the D-shaped insertion part of the endoscope to be covered relative to the position of the inlet aperture formed in the inlet portion of the endoscope cover. What is required in this technique is only to place an endoscope cover on the cover holding stage such that tubes provided in the endoscope cover are at the lowest possible position. Thus, an endoscope cover can be attached to an endoscope in accordance with the same attachment process without a problem that the insertion part of an endoscope gets entangled with tubes disposed in the endoscope cover. This leads to a great improvement in the efficiency of the attachment process.

Figure 6:
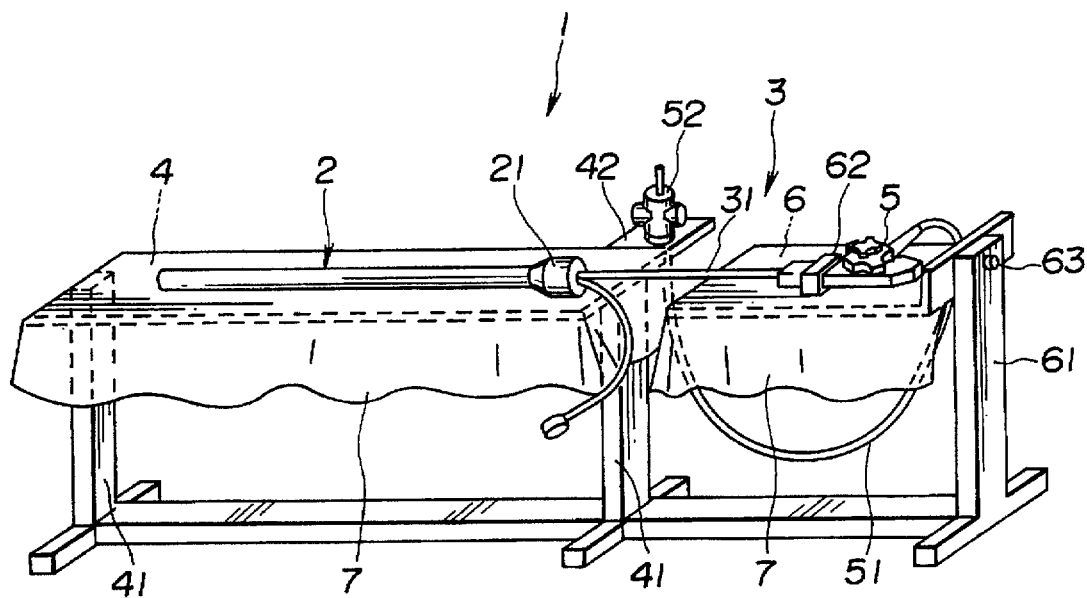
FIG. 6 is a schematic diagram illustrating an endoscope cover attaching apparatus wherein a cover holding stage and an operation part holding stage are covered with a disinfected sheet.

Furthermore, since the space L between the cover holding stage and the operation part holding stage is set to a value greater than the length 1 of the inlet portion, an operator can hold the inlet portion and fit it to the operation part with his/her hand put between the cover holding stage and the operation part holding stage. This makes the fitting operation very easy. Furthermore, as shown in FIG. 6, the cover holding stage 4 and the operation part holding stage 6 may be covered with a disposable disinfected sheet 7 so as to prevent a disinfected endoscope cover 2 and an endoscope 3 to be covered from being contaminated via the cover holding stage 4 and operation part holding stage 6. Thus, the endoscope cover 2 and the endoscope 3 can be maintained clean.

Figure 7:
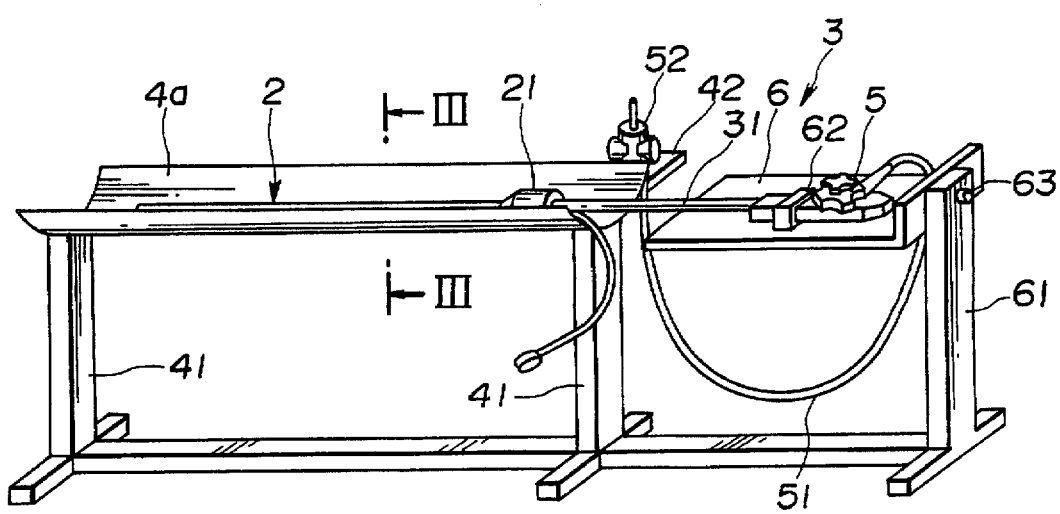
Figures 8A, 8B, 8C:
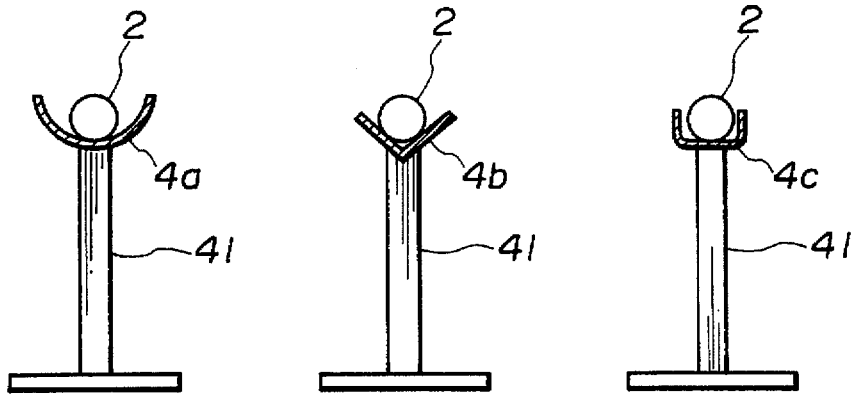
FIG. 8A illustrates a cover holding stage having a semi-circular-shaped cross section.
FIG. 8B illustrates a cover holding stage having a V-shaped cross section.
FIG. 8C illustrates a cover holding stage having a U-shaped cross section.

In the example shown in FIG. 1, the cover holding stage 4 has the form of a flat plane. However, the cover holding stage 4 may also be formed in other various shapes. For example, FIGS. 7 and 8A illustrate a cover holding stage 4a formed in a long and thin shape having a semi-circular shaped cross section. FIG. 8B illustrates a cover holding stage 4b having a V-shaped cross section. In the case of a cover holding stage shown in FIG. 8C, it is formed in a long and thin shape having a U-shaped cross section. With a cover holding stage 4 having such a cross section, an endoscope cover 2 can be easily and instantly placed on the cover holding stage 4 in a stable state such that tubes provided in the endoscope cover come to the lowest possible position keeping its form straight without having a bent portion.

Figure 9:
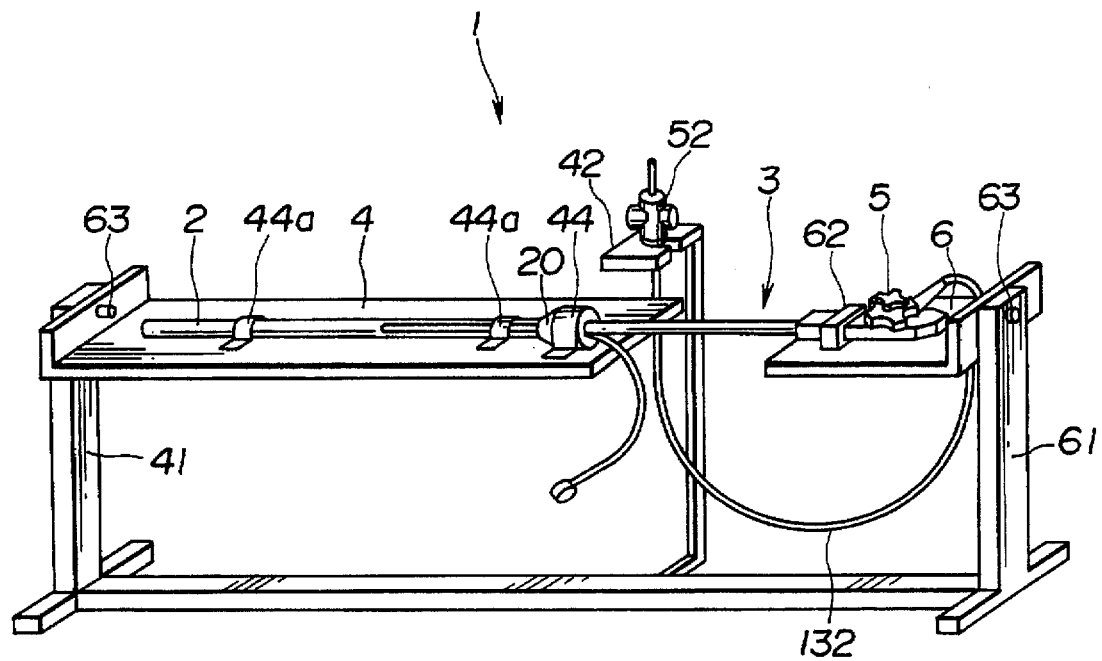
FIG. 9 is a schematic diagram illustrating another structure of an operation part holding stage.

Furthermore, as shown in FIG. 9, the above-described cover holding stage 4 according to the first embodiment may be modified such that its end portion is bent into a L shape and the cover holding stage is supported by a leg 41 via a rotation pin 63 serving as rotation means so that the cover holding stage can rotate around the rotation pin 63 as in the above-described operation part holding stage. However, when the cover holding stage 4 is rotated by the rotation means, the inlet portion 20 and the cover of the endoscope cover 2 move from a proper position. To avoid the above problem, there are provide an inlet portion fixing mechanism 44 and cover holding mechanism 44a on the upper surface of the cover holding stage thereby fixing the inlet portion and the cover portion of the endoscope cover 2 at respective predetermined positions in a detachable fashion. With this arrangement, an endoscope cover 2 is placed on the cover holding stage 4 such that tubes provided in the endoscope cover come to near the lowest possible position, and then the endoscope cover 2 is fixed with the inlet portion fixing mechanism 44 and the cover holding mechanism 44a. Then, the position of the tubes of the endoscope cover is adjusted. Thus, the positioning process of an endoscope cover onto the cover holding stage becomes greatly shortened. In this modified embodiment, no leg is provided at the end portion of the cover holding stage 4 near the operation part holding stage, and therefore a connector holder is formed as a separate element and then connected to the endoscope cover attaching apparatus into an integral form.

Figure 10:
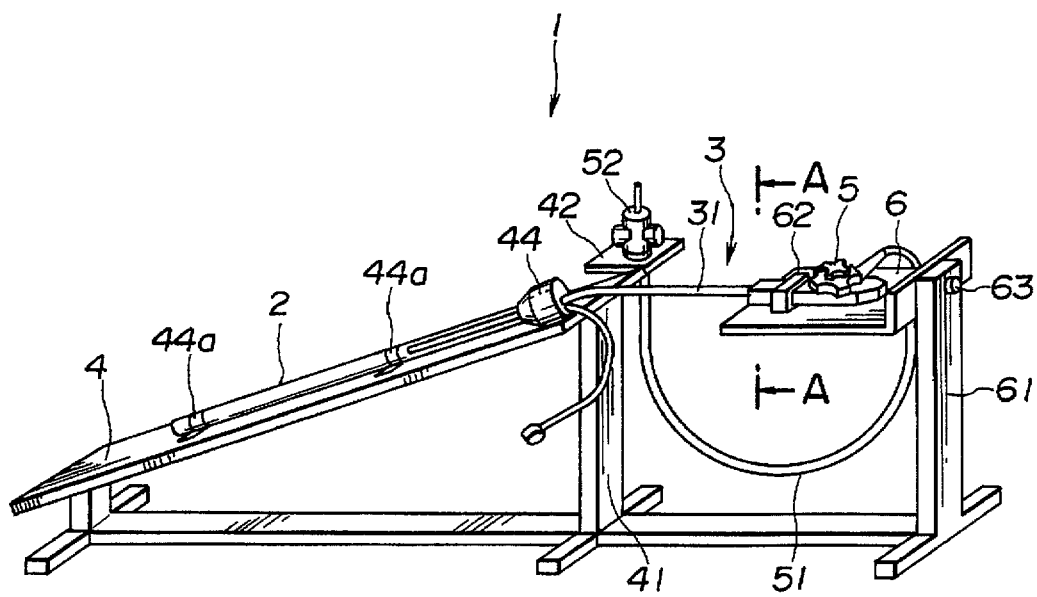
FIG. 10 is a schematic diagram illustrating still another structure of an operation part holding stage.

Furthermore, as shown in FIG. 10, the above-described cover holding stage 4 according to the first embodiment may be modified such that the leg 41 disposed at the outer end of the cover holding stage 4 is shortened so that the cover holding stage lies at an angle greater than 90° relative to the vertical direction. With this arrangement, the total length of the cover holding stage in the horizontal direction can be shortened and thus the endoscope cover attaching apparatus can be installed in less space in an examination room. In this endoscope cover attaching apparatus, there are provided an inlet portion fixing mechanism 44 and a cover holding mechanism 44a on the cover holding stage thereby preventing an endoscope cover from moving from its correct position.

Figure 11:
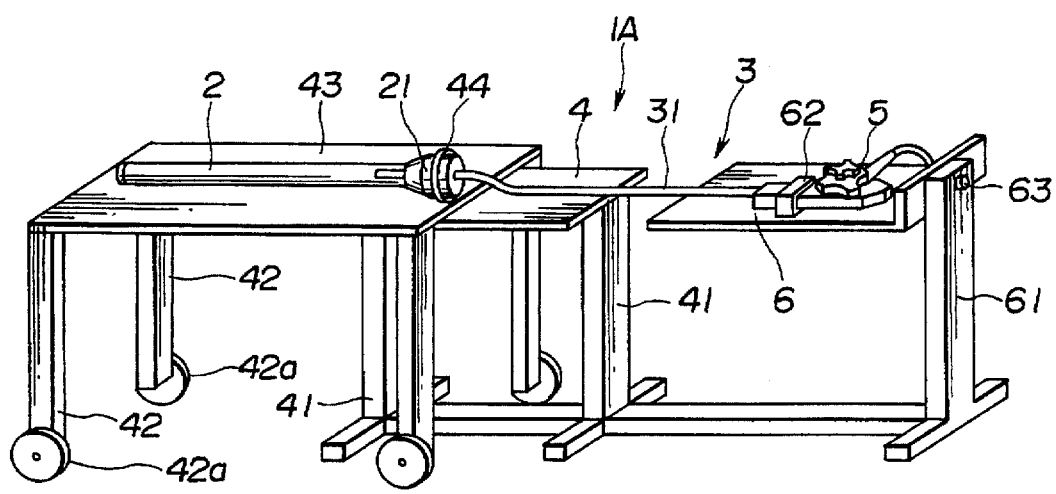
FIG. 11 is a schematic diagram illustrating a second embodiment of an endoscope cover attaching apparatus according to the present invention.

FIG. 11 is a schematic diagram illustrating a second embodiment of an endoscope cover attaching apparatus according to the present invention;

In this embodiment, as shown in the figure, the endoscope cover attaching apparatus 1A includes a sliding stage 43 having legs 42 each provided with a caster 42a wherein the sliding stage 43 is arranged to freely slide over the cover holding stage 4 in the direction parallel to an endoscope cover. On the upper surface of this sliding stage 43 there is provided an inlet portion fixing mechanism 44 for fixing the inlet portion 21 of an endoscope cover 2 onto the sliding stage 43 in a detachable fashion. With the inlet portion fixing mechanism 44, the inlet portion of the endoscope cover does not move relative to the sliding stage during a sliding operation of the sliding stage 43. The other elements and related construction are the same as in the first embodiment described above. These elements are denoted by the same reference numerals as those in the first embodiment, and these will not be described here again.

The endoscope cover attaching apparatus 1A arranged in the above-described manner functions as follows.

First, an endoscope cover 2 is placed on the sliding stage 43 in such a manner that tubes provided in the endoscope cover come to the lowest possible position in the vertical direction, and the inlet portion 21 of the endoscope cover 2 is fixed with the inlet portion fixing mechanism 44 keeping the endoscope cover 2 in the form of a straight line without having a bent portion.

The operation part 5 of the endoscope 3 to be covered is then fixed to the operation part holding stage 6 with the operation part fixing mechanism 62. Adjustment is then performed with the rotation means of the operation part holding stage 6 so that the rotational position of the insertion part 31 having a D-shaped cross section of the endoscope 3 to be covered comes to match the rotational position of the inlet aperture 21a formed in the inlet portion 21 of the endoscope cover 2, and the insertion part 31 is placed on the cover holding stage 4 keeping the above condition.

The end portion of the insertion part 31 placed on the cover holding stage 4 is then inserted into the inlet aperture 21a of the inlet portion 21 fixed to the sliding stage 43. The sliding stage 43 is moved toward the operation part holding stage until the end portion of the insertion part 31 reaches the deepest position of the endoscope cover 2. The inlet portion 21 is then fitted and fixed to the operation part 5 into one piece. Thus, the attachment of the endoscope cover to the endoscope is complete.

In this embodiment, as described above, the inlet portion of an endoscope cover is placed on the sliding stage and then the sliding stage is moved so as to attach the endoscope cover to an endoscope to be covered. Thus, in this technique, the endoscope cover can be attached smoothly to the endoscope to be covered without moving the endoscope cover on the cover holding stage. Furthermore, the insertion part of the endoscope to be covered can be placed on the cover holding stage without having a portion dangling toward a floor and thus keeping the insertion part clean. The other functions and advantages of this embodiment are the same as in the first embodiment described above.

Alternatively, as shown in FIG. 12, there may be provided an automatic attachment apparatus 1A' in which the inlet portion 21 of an endoscope cover 2 is held by an inlet portion holding mechanism 45 in a detachable manner, and the inlet portion holding mechanism 45 is moved by a motor 46 so as to attach the endoscope cover 2 to an endoscope 3 to be covered.

This automatic attachment apparatus 1A' has an automatic attachment mechanism comprising an inlet portion holding mechanism 45, motor 46, moving shaft 47, guide plate 48, and guide shaft 49. The moving shaft 47 has a male thread 47a formed on its periphery. One end of the moving shaft 47 is fixed to the shaft of the motor 46, and the other end is supported by a shaft bearing 48a of the guide plate 48 in such a manner that the moving shaft 47 can rotate. The inlet portion holding mechanism 45 has a sliding hole 45a on the inside of which a female thread is formed so that the male thread 47a of the moving shaft 47 may be engaged with the female thread, and also has a guide hole 45b through which the guide shaft 49 passes.

The functions of the automatic attachment apparatus 1A' will be described below.

Figure 12A:
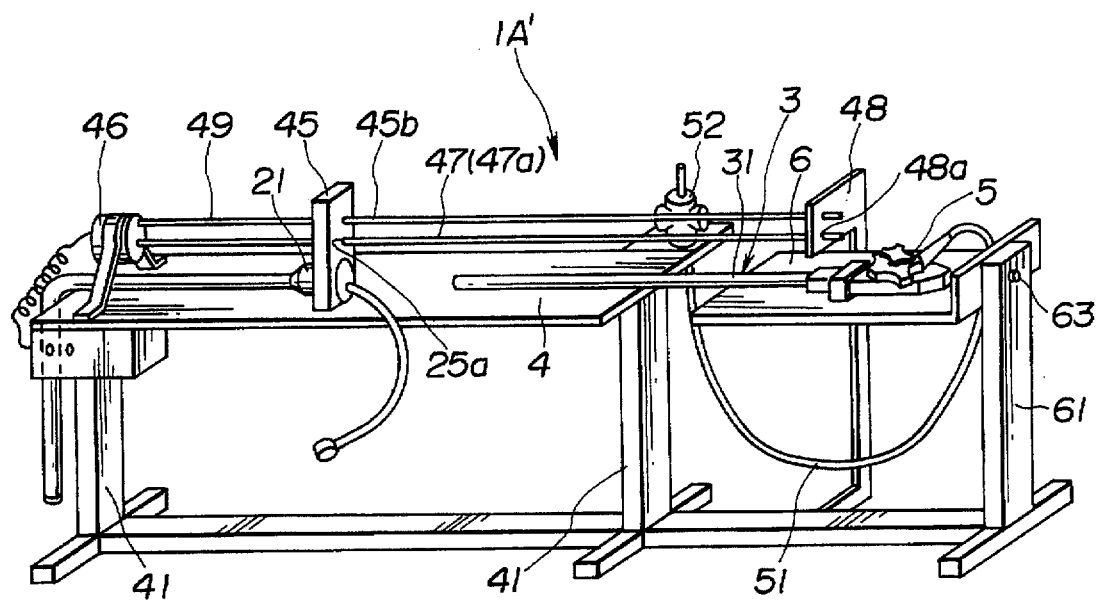
FIG. 12A illustrates a state before the start of an operation of attaching an endoscope cover to an endoscope.

In the initial state of the operation steps for the attachment of an endoscope cover, as shown in FIG. 12A, the inlet portion holding mechanism 45 holding the inlet portion 21 of the endoscope cover 2 is at a position on the back side of the cover holding stage 4 relative to the middle position of the cover holding stage 4, and therefore the cover portion of the endoscope cover dangles from the end of the cover holding stage 4 while the dangling portion has no contact to a floor.

Figure 12B:
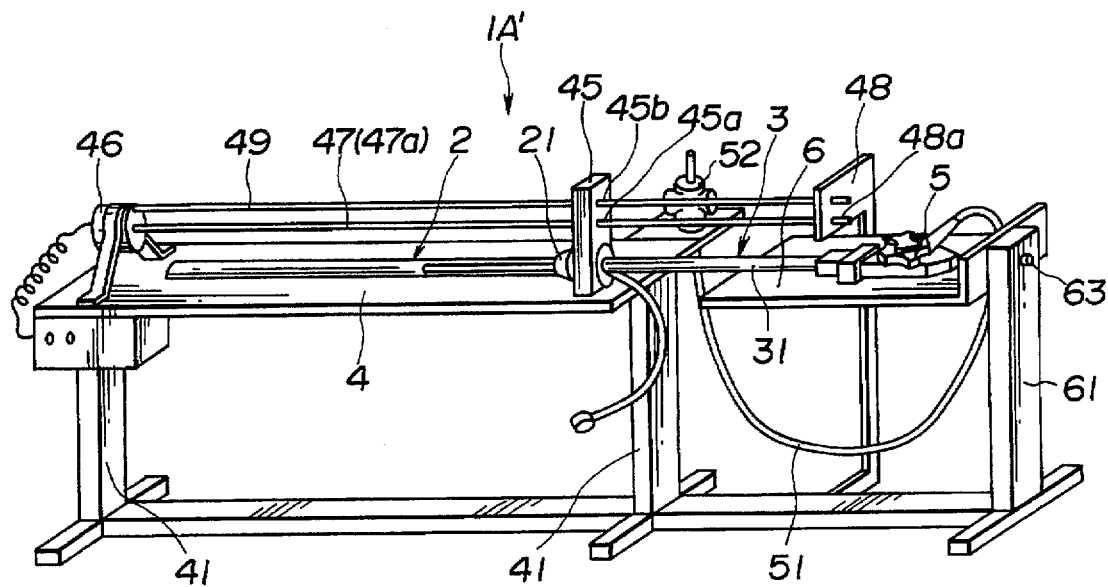
FIG. 12B illustrates a state after the endoscope cover has been attached to the endoscope.

Adjustment is performed so that the rotational position of the insertion part having a D-shaped cross section comes to match the rotational position of the inlet aperture formed in the inlet portion of the endoscope cover. Then, the rotation of the motor 46 of the automatic attachment apparatus 1A' is started. In response to the rotation of the motor 46, the moving shaft 47 is rotated and the inlet portion holding mechanism 45 is moved toward the operation part via the mesh between the male thread 47a formed on the moving shaft 47 and the female thread formed in the sliding hole 45a of the inlet portion holding mechanism 45 as shown in FIG. 12B. The operation part 5 is finally fitted into the inlet portion 21, and the rotation of the motor 46 stops. Thus, the attachment of the endoscope cover 2 to the endoscope 3 to be covered is complete.

Alternatively, an endoscope cover attaching apparatus may also be realized by adding only a guide shaft and inlet portion holding mechanism without employing a moving shaft and a motor. With this arrangement, fine adjustment that will not be achieved by the driving mechanism with a motor is possible in an attachment operation.

Figure 13:
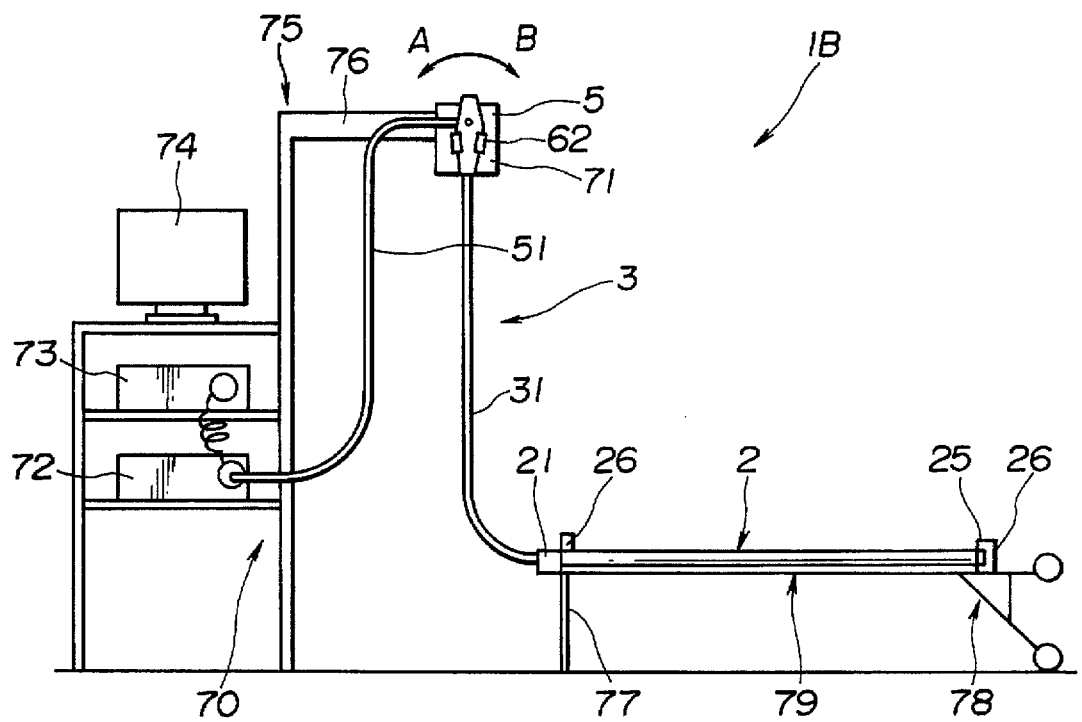

FIGS. 13 and 14 relate to a third embodiment of the present invention, wherein: FIG. 13 is a schematic diagram generally illustrating a structure of an endoscope cover attaching apparatus; and FIG. 14 is a schematic diagram illustrating the operation of the endoscope cover attaching apparatus.

In the present embodiment, as shown in FIG. 13, the endoscope cover attaching apparatus 1B comprises: an operation part holding stage for holding an endoscope in a vertical position, the endoscope having an operation part also serving as a grip of an endoscope and also having an insertion part including an observation optical system; and a cover holding stage capable of holding an insertion part cover and an endoscope cover at an arbitrary angle in the range from 90° to 180° relative to the vertical direction, wherein the endoscope cover includes an insertion part cover for covering the insertion part of the endoscope, and also includes an inlet aperture disposed at an end of the insertion part cover near the hand operation position wherein tubes are disposed in the insertion part cover.

The operation part holding stage 6 includes an operation part holding plate 71 and a scope hanger 75. The operation part 5 of an endoscope 3 to be covered is fixed with the fixing mechanism 62 to the operation part holding plate 71 disposed at the end of the arm 76 of the scope hanger 75, thereby holding the endoscope 3 to be covered in a vertical position.

On the other hand, an endoscope cover 2 is placed on a stand-type cover holding stage 79 in such a manner that the inlet portion 21 and the end portion cover 25 of the endoscope cover 2 are fixed with fixing mechanisms 26 to the stand-type cover holding stage 79 having a post 77 and a leg 78 with a caster, wherein the leg 78 is capable of being folded, and the post and the leg are integral with the cover holding stage 79.

The operation part holding plate 71 is supported by shafts in such a manner that the operation part holding plate 71 can rotate about the axis of the insertion part 31 as well as in directions denoted by arrows A and B in FIG. 13. With this arrangement, the operation part holding plate 71 can be moved to a proper position corresponding to the position of the stand-type cover holding stage 79 on which the endoscope cover 2 is placed, by rotating the operation part holding plate 71 about the axis of the insertion part 31. A universal cord 51 extends from the operation part 5 held by the operation part holding plate 71, and is connected via a connector 52 to a light source 72 installed on a trolley 70. The scope hanger 75 is formed as a part of the trolley 70 on which there are placed the light source 72, a video control unit 73, a monitor 74, etc. The other elements and related construction are the same as in the previous embodiments. These elements are denoted by the same reference numerals as those in the previous embodiments, and these will not be described here again.

The functions of the endoscope cover attaching apparatus 1B configured in the above-described manner will be described below.

First, an endoscope cover 2 is placed on the stand-type cover holding stage 79 in such a manner that tubes (not shown) provided in the endoscope cover 2 come to the lowest possible position. Then, the operation part 5 of an endoscope 3 to be covered is fixed to the operation part holding plate 72 with the fixing mechanism 62 in such a manner so as to hold the endoscope in a vertical position. Furthermore, there is provided rotation means for adjusting the rotational position of the insertion part having a D-shaped cross section of the endoscope to be covered relative to the rotational position of the inlet aperture of the endoscope cover.

The end portion of the insertion part 31 dangling downward in the vertical direction is then inserted into the inlet portion 21 of the endoscope cover 2 via its inlet aperture as shown in FIG. 13.

Figure 14A:
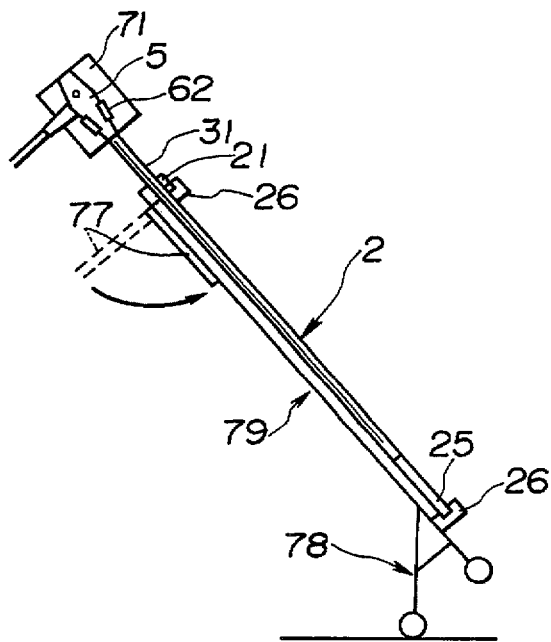
FIG. 14A illustrates a state in which an insertion part is being inserted into an endoscope cover.

The end portion of the stand-type cover holding stage 79, at which the post 77 is disposed and at which the inlet portion 21 of the endoscope cover 2 is fixed, is held by a hand and moved, together with the endoscope cover held on it, gradually from a position at 90° to a position at 180° relative to the vertical direction thereby inserting the insertion part 31 into the endoscope cover 2 as shown in FIG. 14A. At the beginning of the above operation, the post 77 is folded toward the cover holding stage.

Figure 14B:
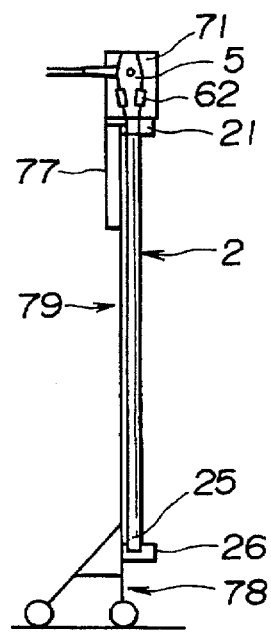
FIG. 14B illustrates an cover holding stage placed in a vertical position.

After the stand-type cover holding stage 79 has come to a vertical position, the operation part 5 is fitted and fixed to the inlet portion 21 into an integral form as shown in FIG. 14B, and thus the attachment of the endoscope cover 2 to the endoscope 3 to be covered is complete. In this state, the fixing mechanism 26 fixing the inlet portion 21 to the end portion cover 25 is unfastened and the stand-type cover holding stage 79 is removed from the endoscope cover 2.

When the endoscope cover has been attached to the endoscope to be covered by fixing the operation part of the endoscope to be covered to the operation part holding plate disposed on the scope hanger of the trolley, the covered-type endoscope has become ready for use. The other functions and advantages of this embodiment are the same as in the previous embodiments described above.

Figure 15A:
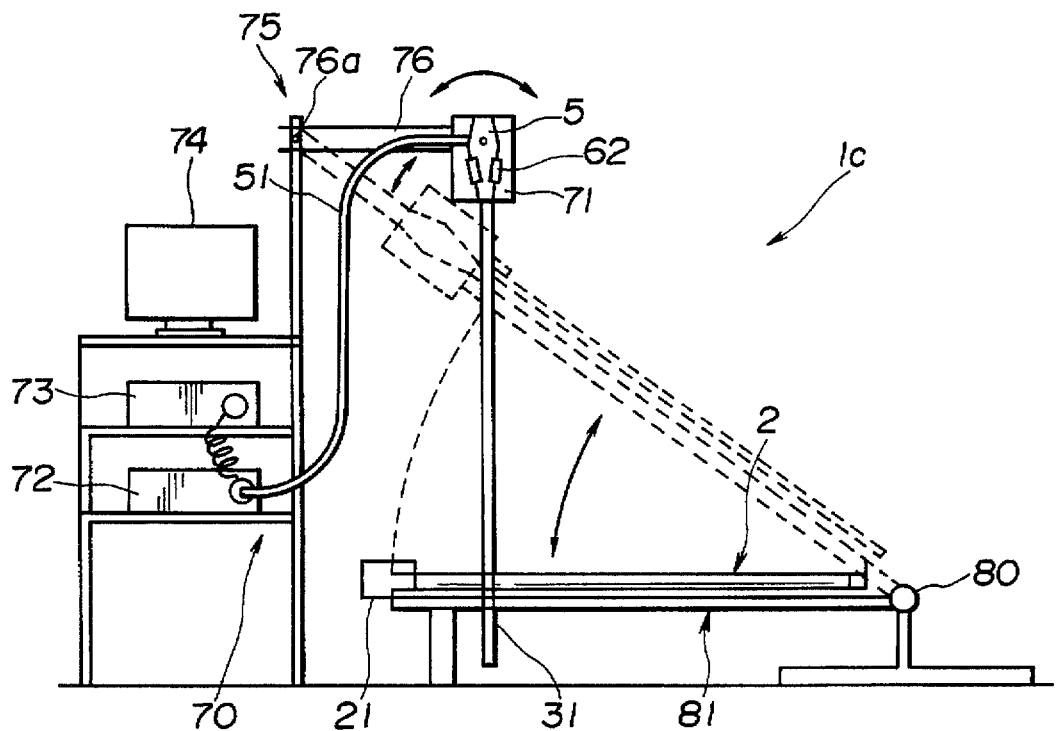
FIG. 15A illustrates the operation of the endoscope cover attaching apparatus.

FIG. 15 is a schematic diagram illustrating a fourth embodiment of an endoscope cover attaching apparatus according to the present invention.

In the endoscope cover attaching apparatus 1C according to this embodiment, as shown in FIG. 15, the arm 76 of the scope hanger 75 disposed on the trolley 70 is arranged to rotate about the rotation axis 76a of the arm as illustrated by the arrows in the figure. Furthermore, the cover holding stage 81 on which an endoscope cover 2 is to be placed is arranged to rotate about the rotation shaft 80 of the cover holding stage. The rotation shaft 80 of the cover holding stage has a ratchet mechanism whereby once the cover holding stage's end portion at which the inlet portion is placed is moved upward by rotation, the cover holding stage will not return to the original position unless a release button (not shown) is pressed. The movement of the arm 76 of the scope hanger 75 around the rotation shaft 76a of the arm is also based on a ratchet mechanism as in the movement around the rotation shaft 80 of the cover holding stage, and thus, in a normal state, the arm 76 can move only downward by rotation around the rotation shaft 76a of the arm. The other elements and related construction are the same as in the third embodiment described above. These elements are denoted by the same reference numerals as those in the third embodiment, and these will not be described here again.

The functions of the endoscope cover attaching apparatus 1C configured in the above-described manner will be described below.

First, the insertion part 31 of an endoscope 3 to be covered is inserted into the inlet portion 21 of an endoscope cover 2. The rotary-type cover holding stage 81 is then gradually moved upward by rotation from a position at 90° relative to the vertical direction to a position at a greater angle. Then, the arm 76 is gradually moved downward by rotation thereby inserting the endoscope 3 to be covered into the endoscope cover 2, until both insertion part 31 of the endoscope 3 to be covered and endoscope cover 2 come to lie on the same straight line. When the operation part 5 of the endoscope 3 to be covered, the insertion part 31, and the endoscope cover 2 have come to the position at which all these element are held on a slanted straight line, the attachment operation is complete.

In this embodiment, as described above, the rotary-type cover holding stage on which an endoscope cover is placed is adapted to rotate about the rotation shaft of the cover holding stage, and the arm of the scope hanger is also adapted to rotate about the rotation shaft of the arm. This arrangement allows connection between the operation part and inlet portion to be performed at a lower position, and thus allows an even short person to do a connecting operation at his/her breast position. The other functions and advantages of this embodiment are the same as in the previous embodiments described above.

Figure 15B:
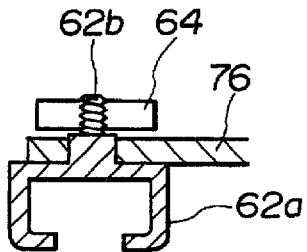
FIG. 15B illustrates another structure of a fixing mechanism for fixing a operation part.
Figure 15C:
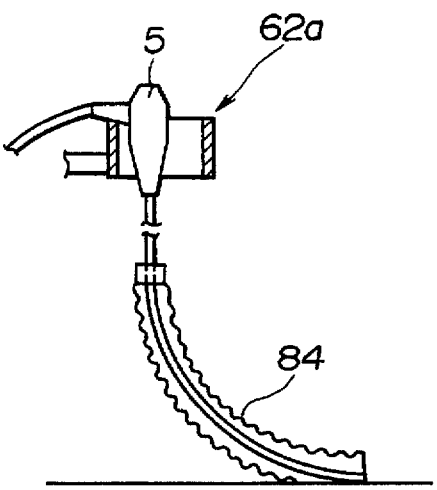
FIG. 15C illustrates still another structure of a fixing mechanism for fixing an operation part.

In an alternative embodiment, the fixing mechanism 62 for fixing the operation part 5 is modified into a U-shaped fixing mechanism 62a as shown in FIG. 15B. In this arrangement, the fixing mechanism 62a is fixed, in a free fit fashion, to the arm 76 with a screw 62b disposed on the fixing mechanism 62a and with a nut 64 engaged with the screw 62b in such a manner that the fixing mechanism 62a can rotate. In this case, the operation part holding plate 71 is no longer necessary. Alternatively, as shown in FIG. 15C, the U-shaped portion of the fixing mechanism may be arranged such that the U-shaped portion has a width greater than that of the operation part and holds a folding stopper made up of an elastomeric material whereby the operation part can rotate without having a free-fit mechanism.

Figure 16:
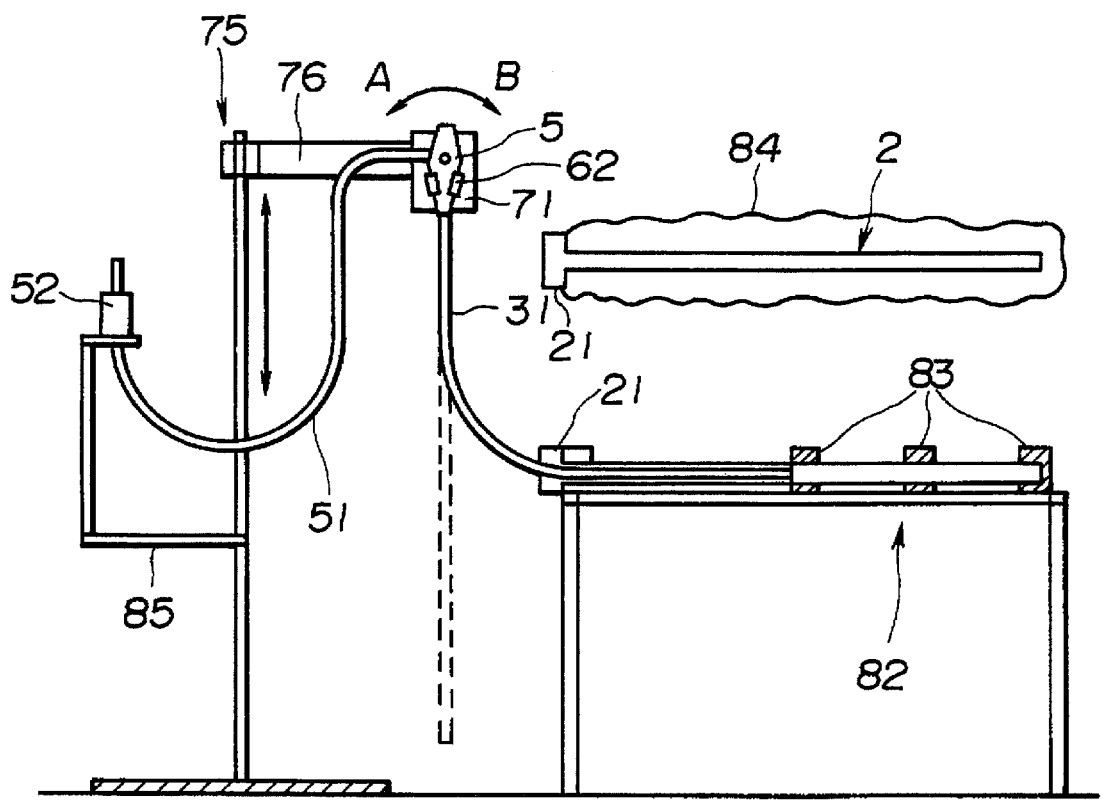
Figure 17:
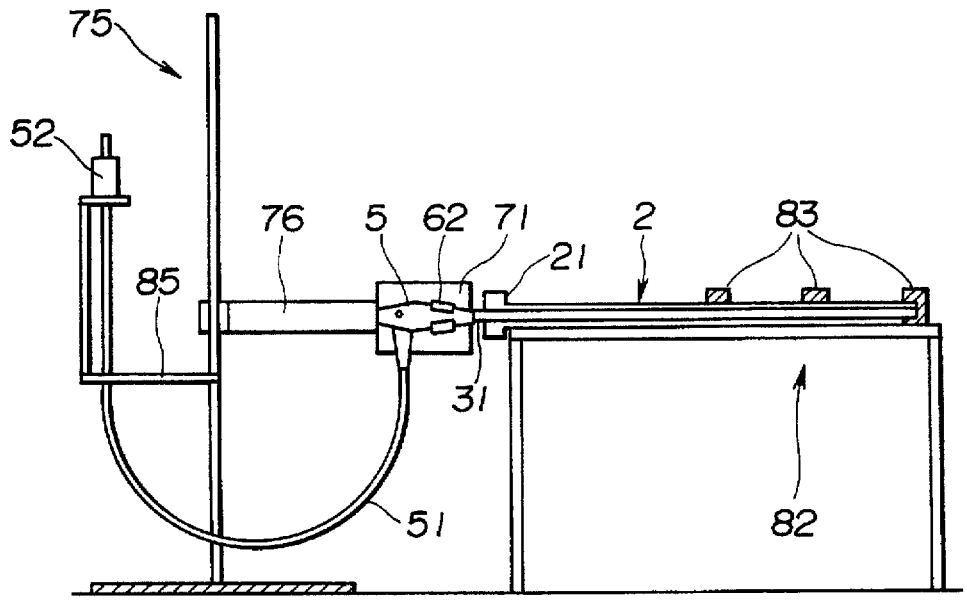

FIGS. 16 and 17 relate to a fifth embodiment of the present invention, wherein: FIG. 16 is a schematic diagram generally illustrating a structure of an endoscope cover attaching apparatus; and FIG. 17 is a schematic diagram illustrating a state in which an endoscope cover has been attached to an endoscope using the endoscope cover attaching apparatus.

In this embodiment, as shown in FIG. 16, the arm 76 of the scope hanger 75 is arranged to be movable up and down as illustrated by the arrows in the figure. An endoscope cover 2 is placed on the cover holding stage 82 disposed at a rather high position. The cover holding stage 82 has a plurality of end portion cover fixing mechanisms 83 for fixing the end portion cover 25 of the endoscope cover 2. This arrangement makes it possible to fix any type of endoscope cover 2 whose length varies depending on its type. With this arrangement, furthermore, even an endoscope cover 2 covered with an over-tube 84 can be placed on the endoscope cover attaching apparatus without having to remove the over-tube 84.

The scope hanger 75 has a connector holder 85 for holding the connector 52 disposed at the end of the universal cord 51 extending from the endoscope 3 to be covered. The other elements and related construction are the same as in the third embodiment described above. These elements are denoted by the same reference numerals as those in the third embodiment, and these will not be described here again.

In the endoscope cover attaching apparatus according to this embodiment, as described above, the insertion part 31 of an endoscope 3 to be covered is first inserted into the inlet portion 21 of an endoscope cover 2, and then the arm 76 is gradually moved downward thereby inserting the insertion part 31 further into the cover via the inlet portion 21. When the supporting arm 76 has reached a position at nearly the same height as the endoscope cover 2, the operation part 5 fixed to the operation part holding plate 71 is rotated toward the endoscope cover as shown in FIG. 17. Thus, the attachment operation is complete. As can be seen from the above description, the present embodiment provides functions and advantages similar to those obtained in the previous embodiments.

Figure 18:
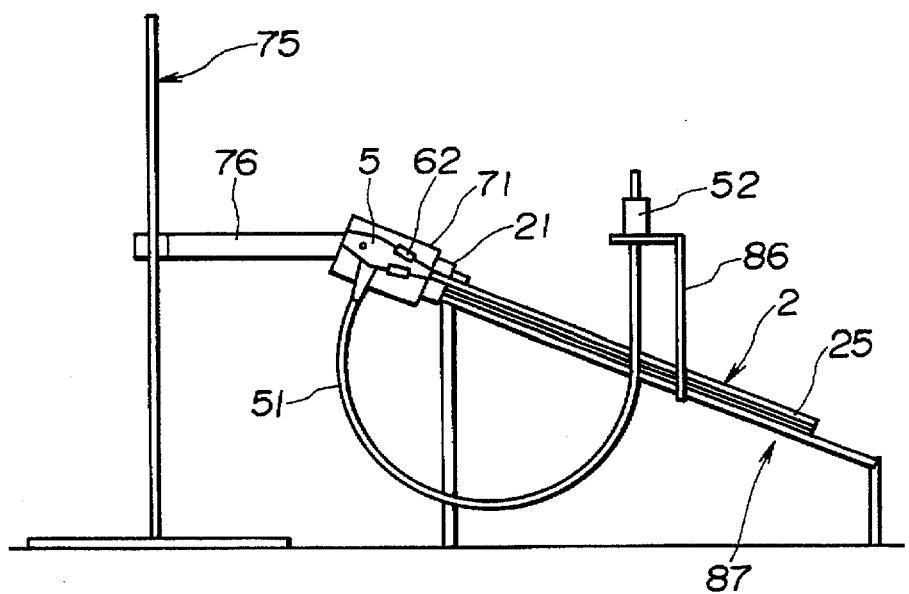
FIG. 18 is a schematic diagram generally illustrating an endoscope cover attaching apparatus whose structure is partially different from that of the fifth embodiment.

Alternatively, a connector holder 86 may be disposed on a cover holding stage 87, and the cover holding stage 87 may be disposed at a slanted position as shown in FIG. 18 thereby making it easier to smoothly insert the insertion part 31 of an endoscope 3 to be covered into an endoscope cover 2.

Figure 19:
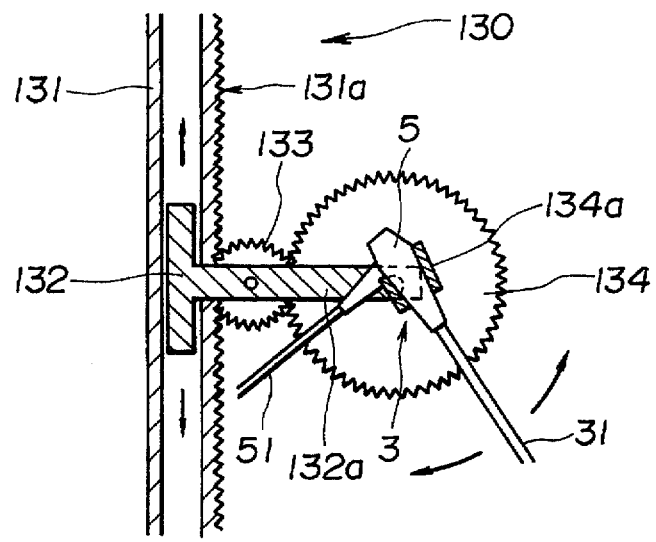
FIG. 19 is a schematic diagram illustrating another structure of a scope hanger.

As for the scope hanger 75 for moving the arm 76 up and down, a scope hanger 130 such as that shown in FIG. 19 may also be employed. In this case, as shown in this figure, the scope hanger 130 comprises: a post 131 having a rack 131a; a slider 132 adapted to move along the post 131 up and down; a pinion 133 disposed on an arm 132a extending form the slider 132, the pinion 133 engaging with the rack 131a formed on the post 131; and a gear 134 coupled with an operation part holder 134a for holding the operation part 5 of an endoscope 3 to be covered, wherein the gear 134 engages with the pinion 133.

In the scope hanger 130 having the structure described above, if the operation part 5 held by the operation part holder 134a connected to the gear 134 is rotated in a direction (horizontal direction) denoted by the arrow A in FIG. 19, then the gear 134 rotates while engaging with the pinion 133 which in turn engages with the rack 131a and thus the slider 132 moves downward along the post 131. Conversely, if the operation part 5 is rotated in the opposite direction (vertical direction) denoted by the arrow B in FIG. 19, then the gear 134 rotates in the opposite direction while engaging with the pinion 133 which in turn engages with the rack 131a and thus the slider 132 moves upward along the post 131. When the operation part 5 of the endoscope 3 to be covered is in a vertical position, the slider 132 comes to the highest possible position on the post 131 at which the insertion part 31 is at a position farthest from a floor.

As described above, in an operation of attaching an endoscope cover to an endoscope to be covered using the endoscope cover attaching apparatus, the operation part of the endoscope to be covered can be moved to the lowest possible position along the post only by horizontally moving (in a direction denoted by the arrow A) the operation part held by the operation part holder of the rack hanger. Therefore, the insertion part can be inserted smoothly into the endoscope cover. Furthermore, the operation part can be easily fitted to the inlet portion of the endoscope cover.

After the completion of the attachment of the endoscope cover, if the endoscope covered with the endoscope cover is moved back to the vertical position, the slider moves along the post to the highest possible position, and thus the insertion part can be held at a position far from the floor.

Figure 20:
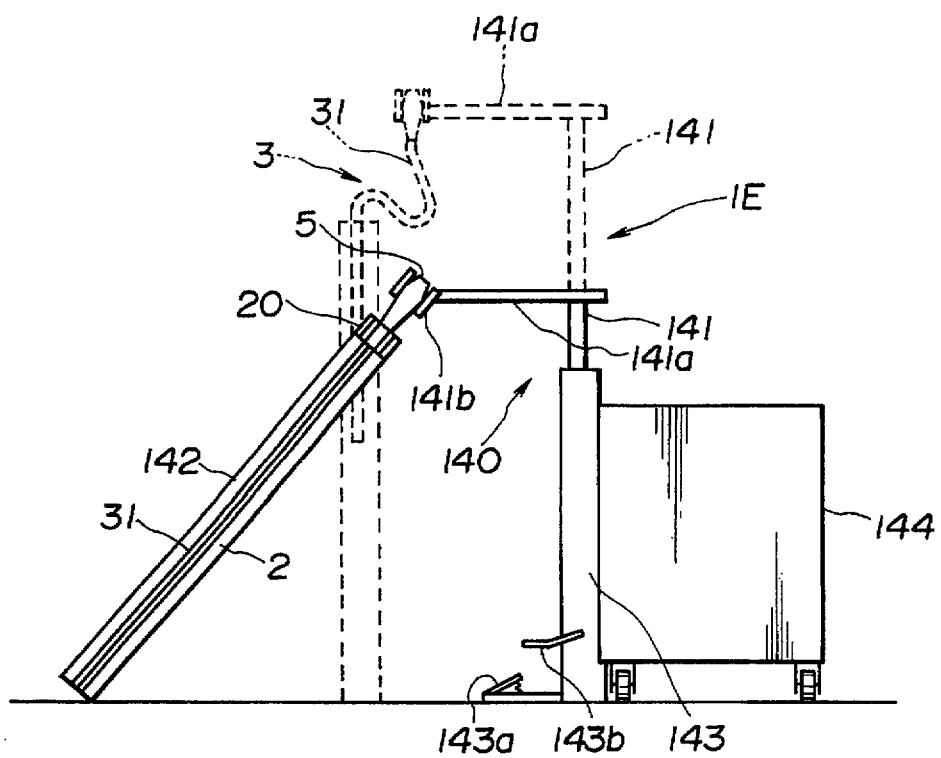
FIG. 20 is a schematic diagram illustrating a sixth embodiment of an endoscope cover attaching apparatus according to the present invention.

FIG. 20 is a schematic diagram illustrating a sixth embodiment of an endoscope cover attaching apparatus according to the present invention.

In this embodiment, the endoscope cover attaching apparatus 1E comprises, as shown in FIG. 20, an operation part holding stage 140 having a post 141 adapted to move up and down by means of a hydraulic cylinder, and a cover holding stage 142 that also serves as an endoscope cover package.

A supporting arm 141a is disposed at the upper end of the post 141 of the operation part holding stage 140. An operation part holder 141b is disposed at the end of the supporting arm 141a in such a manner that the operation part holder 141b can rotate. The operation part 5 of an endoscope 3 to be covered is held by the operation part holder 141b. The operation part 5 held by the operation part holder 141b can be moved up and down by using the hydraulic cylinder 143 provided on the operation part holding stage 140. In this endoscope cover attaching apparatus 1, the operation part holding stage 140 having the hydraulic cylinder 143 is disposed in an integral fashion on a cart 144 on which a light source and a video control unit are also disposed. The hydraulic cylinder 143 of the operation part holding stage 140 has a compression pedal 143a and a compression release pedal 143b used to move the post 141 up and down. Furthermore, the cover holding stage 142 also acts as a package for packing an endoscope cover 2. The supporting arm 141a has a length long enough to ensure that a vertically-dangling part of the insertion part 31 held by the operation part holder 141b will have no contact to the cart 144 even when the insertion part 31 moves to a certain degree.

In this endoscope cover attaching apparatus 1E having the structure described above, the post 141 can be raised from a lower position toward an upper position by pressing a few times the compression pedal 143a of the hydraulic cylinder 143. Conversely, the post 141 can be lowered from an upper position down to a lower position by pressing a few times the compression release pedal 143b of the hydraulic cylinder 143.

In a state in which the operation part holder 141b is held at an upper position illustrated by broken lines in FIG. 20, an operation of attaching the endoscope cover 2 to the endoscope 3 to be covered is started, and the compression release pedal 143b is pressed repeatedly so as to lower the post 141 thereby gradually inserting the insertion part 31 into the endoscope cover. In the above operation, the cover holding stage 4, that also acts as the package in which the endoscope cover 2 is packed, is held in a slanted position. When the operation part holder 141b reaches the lower position, the insertion part 31 has been completely inserted into the endoscope cover 2 and the operation part 5 is fitted to the inlet portion 20. Then, the compression pedal 143a is pressed a few times so as to raise the operation part 5 to the upper position. The endoscope cover 2 is then removed from the cover holding stage 4 also acting as the package. Thus, the attachment operation is complete.

In an operation of attaching an endoscope cover to an endoscope to be covered using the above endoscope cover attaching apparatus having the hydraulic cylinder, the operation part holding stage can be moved up and down only by the operation with an operator's foot while maintaining both hands free. Thus, an endoscope cover can be easily attached to an endoscope to be covered with greater operation efficiency. Furthermore, since the cover holding stage also serves as a package for packing an endoscope cover, it is possible to easily maintain the endoscope cover clean until the attachment operation.

In the above embodiments, the arm 76 and the supporting arm 141a have a great enough length to ensure that these element will have no contact to the cart or the trolley thereby preventing these element from being contaminated even if the insertion part dangling downward moves to a certain degree. However, this means that the arm 76 and the supporting arm 141a extend a rather long distance from the cart or the trolley, and thus these extending elements may cause inconvenience in keeping the endoscope cover attaching apparatus in a small space or in transferring it to another place.

Figure 21A:
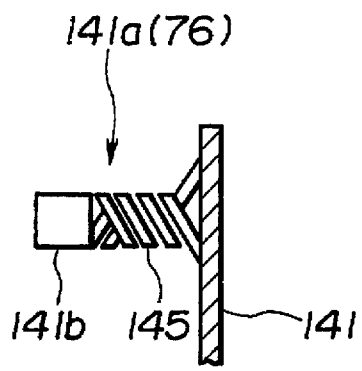
FIG. 21A illustrates an arm capable of being expanded and contracted wherein the arm is in a contracted state in this figure.
Figure 21B:
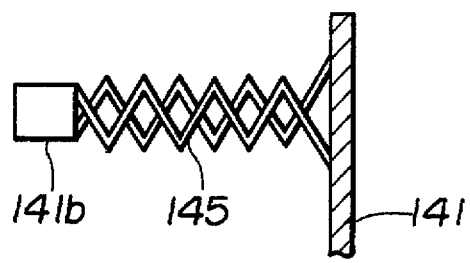
FIG. 21B illustrates the arm capable of being expanded and contracted wherein the arm is in an expanded state in this case.
Figure 22A:
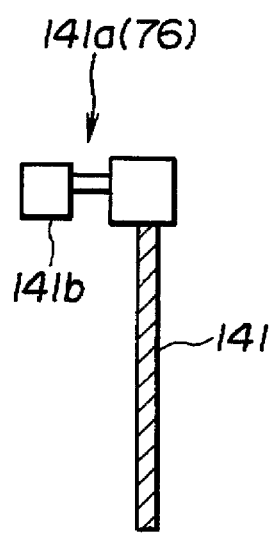
FIG. 22A illustrates an arm capable of being expanded and contracted wherein the arm is in a contracted state in this figure.
Figure 22B:
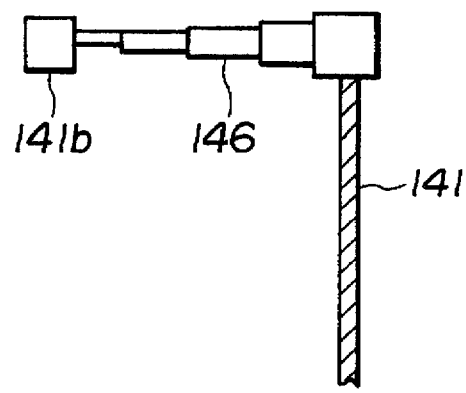
FIG. 22B illustrates the arm capable of being expanded and contracted wherein the arm is in an expanded state in this case.

This problem can be avoided by forming the supporting arm 141a with a plurality of links 145 linked to each other in such a manner that the supporting arm 141a can expand and contract in a horizontal direction, as shown in FIG. 21. With this arrangement, when the operation part 5 of an endoscope 3 to be covered is held by the operation part holder 141b, the links 145 are expanded as shown in FIG. 21B so that the insertion part 31 of the endoscope 3 to be covered comes to a position apart enough from the cart 144 and other elements. On the other hand, when the operation part holder 141b holds nothing, the links 145 can be contracted to a position near the cart 144. Therefore, it becomes possible to easily keep the endoscope cover attaching apparatus in a small space or transfer it to another place.. The supporting arm 141a is not limited to the above-described example composed of the links 145. The supporting arm 141a may also be composed of a plurality of sleeves 146, 146 . . . , having different diameters which are linked to each other and thus combined together in such a manner that the supporting arm 141a can expand and contract, as shown in FIG. 22.

Figure 23:
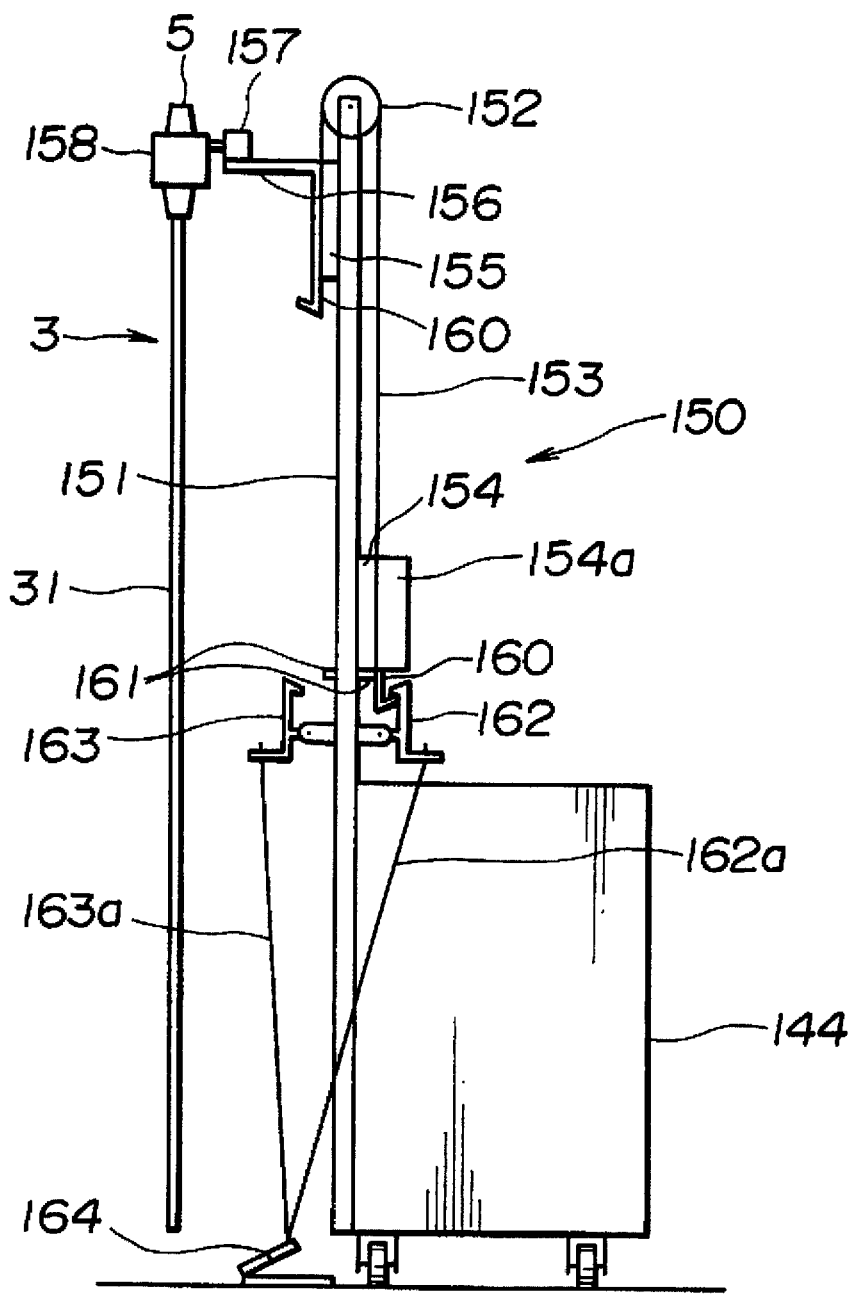
Figure 24:
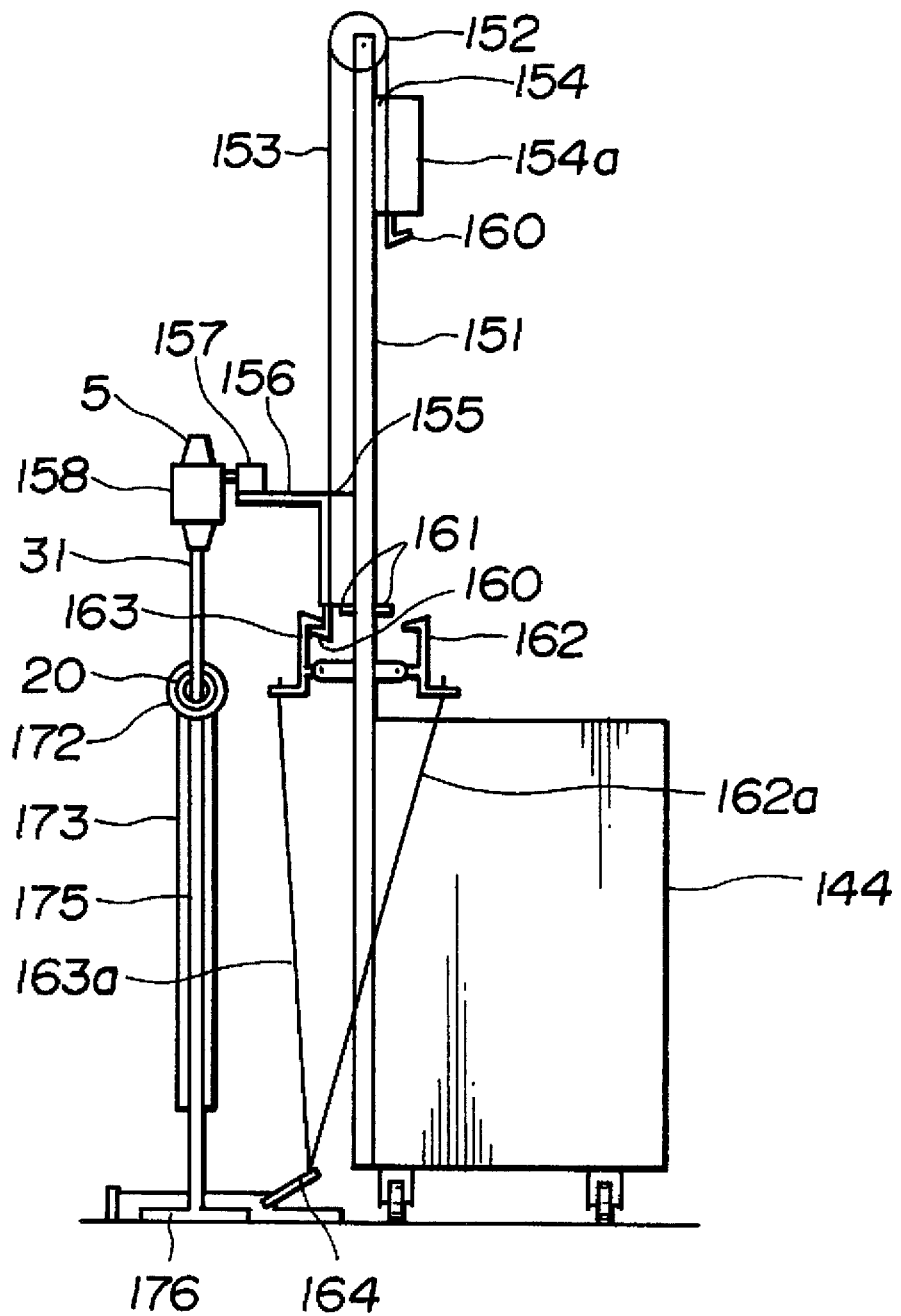
Figure 25:
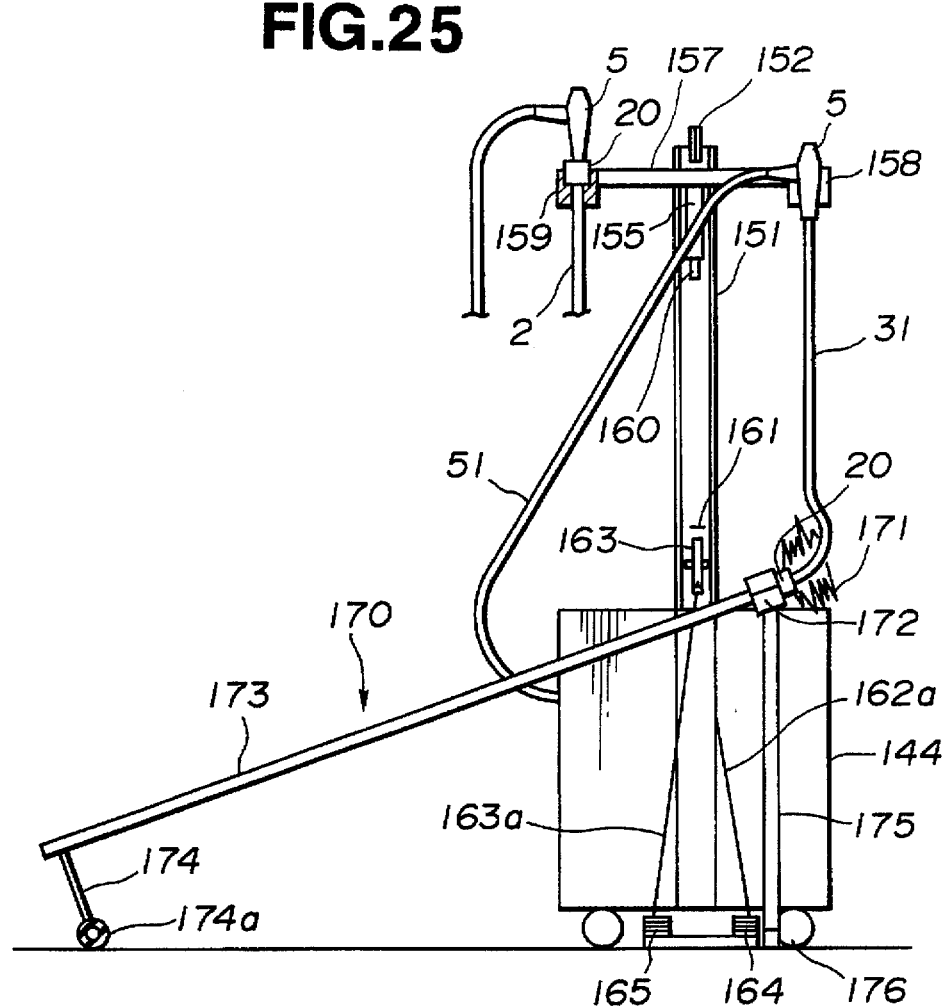

FIGS. 23 to 25 relate to a seventh embodiment of the present invention, wherein: FIG. 23 is a side view illustrating a general structure of an operation part holding stage; FIG. 24 is a side view illustrating a state in which the insertion part of an endoscope is being inserted into an endoscope cover; and FIG. 25 is a front view of FIG. 24.

In the endoscope cover attaching apparatus 1F according to this embodiment, as shown in these figures, a post 151, which is one of elements composing an operation part holding stage 150, is fixed to a cart 144 in an integral form. A pulley 152 is disposed at the upper end of the post 151, and a wire 153 is hung from the pulley 152.

One end of the wire 153 is connected to an inside slider 154 that moves up and down on a rail disposed on the post 151 on the side nearer to the cart. The other end of the wire 153 is connected to an outside slider 155 that moves up and down on a rail disposed on the post 151 on the side opposite to the cart 144. The outside slider 155 has a supporting arm 156. A hanger supporting pipe 157 is provided on the supporting arm 156. The supporting arm 156 also has a second hanger 158 for fixing the operation part 5 to the hanger supporting pipe 157, and a first hanger 159 for fixing the inlet portion 20.

A hook 160 is formed at the lower end of the inside slider 154 and also at the lower end of the outside slider 155. A stopper 161 is disposed in the middle of each rail disposed on the respective sides of the post 151 nearer to and opposite to the cart. These stoppers 161 are used to stop each slider at the lowest position. When the inside slider 154 reaches the lowest position and comes in contact with the stopper 161, the hook 160 is locked by an inner pawl 162 thereby holding the inside slider 154. The inner pawl 162 includes a spring which produces force toward the post. When the inside slider 154 moves downward from the upper position and as a result the hook 160 comes in contact with the inner pawl 162, the inner pawl 162 moves on the slanted plane of the hook 160, and the force of the spring acts so that the hook 160 is locked by the inner pawl 162 just before the inside slider 154 reaches the stopper 161. Thus, the inside slider 154 is fixed. Similarly, the outside slider 155 is fixed with the hook 160 locked by the outer pawl 163 at a position at which the outside slider 155 reaches the stopper 161. The outer pawl 163 has a structure similar to that of the inner pawl 162 described above, and has a relationship to the hook 160 and the stopper 161 similar to that in the case of the inner pawl 162, while these will not be described here again.

The inside slider 154 has a weight 154a so that when the endoscope 3 to be covered is held by either the first hanger 159 or the second hanger 158, the inside slider 154 becomes slightly heavier than the outside slider 155. In this structure, a very small load is applied to the outside slider 155 so as to maintain a balance between the outside slider 155 and the inside slider 154. That is, in a situation in which the inside slider 154 is not locked by the inner pawl 162 and also in a situation in which the outside slider 155 is not locked by the outer pawl 163, the first hanger 159 or the second hanger 158 moves upward at a slow speed while carrying an endoscope 3 to be covered. However, if the insertion part 31 is pulled downward by very weak force with a hand, the first hanger 159 and second hanger 158 move downward.

The length of the wire 153 is set to such a value that when the outside slider 155 comes to the lowest position, the inside slider 154 comes to the highest position, and conversely, when the inside slider 154 comes to the lowest position, the outside slider 155 comes to the highest position.

Furthermore, the inner pawl 162 is connected to an inner wire 162a, which is in turn connected to an H-pedal 164. Similarly, the outer pawl 163 is connected to an outer wire 163a, which is in turn connected to an L-pedal 165. In this structure, if the H-pedal 164 is pressed by a foot, the inner pawl 162 is pulled via the inner wire 162a in the direction opposite to the post. As a result, the inner pawl 162 moves against the force of the spring and the lock between the hook 160 and the inner pawl 162 is relieved. Similarly, if the L-pedal 165 is pressed by a foot, the outer pawl 163 is pulled via the outer wire 163a in the direction opposite to the post, and thus the outer pawl 163 moves against the force of the spring and the lock between the hook 160 and the outer pawl 163 is relieved.

In this embodiment, the cover holding stage 170 holds an endoscope cover 2 at a position having an angle of 90° or greater relative to the vertical direction. The inlet portion 20 of the endoscope cover 2 is provided with a universal cord 51 for use in connection with an endoscope to be covered as well as a universal cord cover 171 for covering the operation part 5.

The cover holding stage 170 includes: an inlet portion holder 172 for holding the inlet portion 20 of the endoscope cover, and an insertion part cover holder 173 for holding a cover that covers the insertion part 31. At the end of the insertion part cover holder 173, there is provided a short leg 174 having a caster 174a so that the cover holding stage 170 can be moved to a vertical position when the cover holding stage 170 is kept. The inlet portion holder 172 has a long leg 175 at its lower end.

The functions of the endoscope cover attaching apparatus 1F having the structure described above will be described below.

In a situation in which the endoscope cover attaching apparatus 1F is kept, or in a preparatory step for attaching an endoscope 3 to be covered to an endoscope cover 2, the hanger supporting pipe 157 having the first hanger 159 and second hanger 158 is at the highest position so that the end portion of the insertion part 31 of the endoscope 3 to be covered is kept apart from a floor, as shown in FIG. 23.

In the first step of attaching the endoscope cover 2 to the endoscope 3 to be covered, the end portion of the vertically-dangling insertion part 31 of the endoscope 3 to be covered, which includes an observation optical system such as an image fiber or a solid state image sensor, is inserted into the endoscope cover 2 via the inlet portion 2C as shown in FIG. 23.

The H-pedal 164 is then pressed by a foot so as to relieve the lock of the inside slider 154. The insertion part 31 is pulled down to the lower position thereby inserting the insertion part 31 into the endoscope cover as shown in FIGS. 24 and 25, and then the operation part is fitted to the inlet portion. At this stage, the hanger supporting pipe 157 having the first hanger 159 and the second hanger 158 has come to the lower position.

As described above, although the endoscope to be covered can be moved downward by very weak force, if the endoscope to be covered is relieved from a hand, then the hanger supporting pipe 157 moves upward carrying the endoscope to be covered held by either the first hanger 159 or the second hanger 158. This leads to an improvement in the efficiency of the attachment operation of an endoscope cover. The other functions and advantages of this embodiment are the same as in the previous embodiments described above.

In this embodiment, the first hanger 159 and the second hanger 158 are provided on the hanger supporting pipe 157 in such a manner that they have a holding position different from each other. Therefore, the position of the end portion of the insertion part relative to the floor is also different between the first and second hangers. This problem can be solved by a modified embodiment shown in FIG. 26 in which a modified supporting pipe 157a is employed as the hanger supporting pipe 157.

Figure 26:
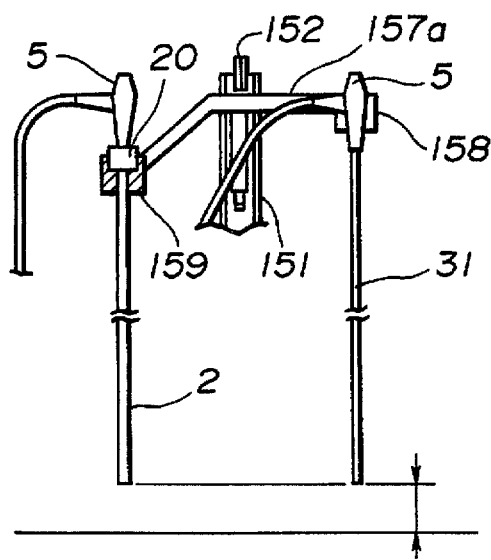
FIG. 26 is a schematic diagram illustrating a modified example of a hanger supporting pipe.

In this modified supporting pipe 157a, the second hanger 158 for holding the operation part 5 and the first hanger 159 for holding the inlet portion 20 are disposed, as shown in FIG. 26, at a height different from each other so that the operation part 5 of the endoscope 3 to be covered which is held by the first hanger 159 and the operation part 5 held by the second hanger 158 are located at the same height. Thus, in either case in which the endoscope 3 covered with the endoscope cover 2 is held by the first hanger 159 or the endoscope 3 to be covered is held by the second hanger 158, the distance from the floor to the end of the endoscope cover is always the same as the distance from the floor to the end of the insertion part.

Figure 27:
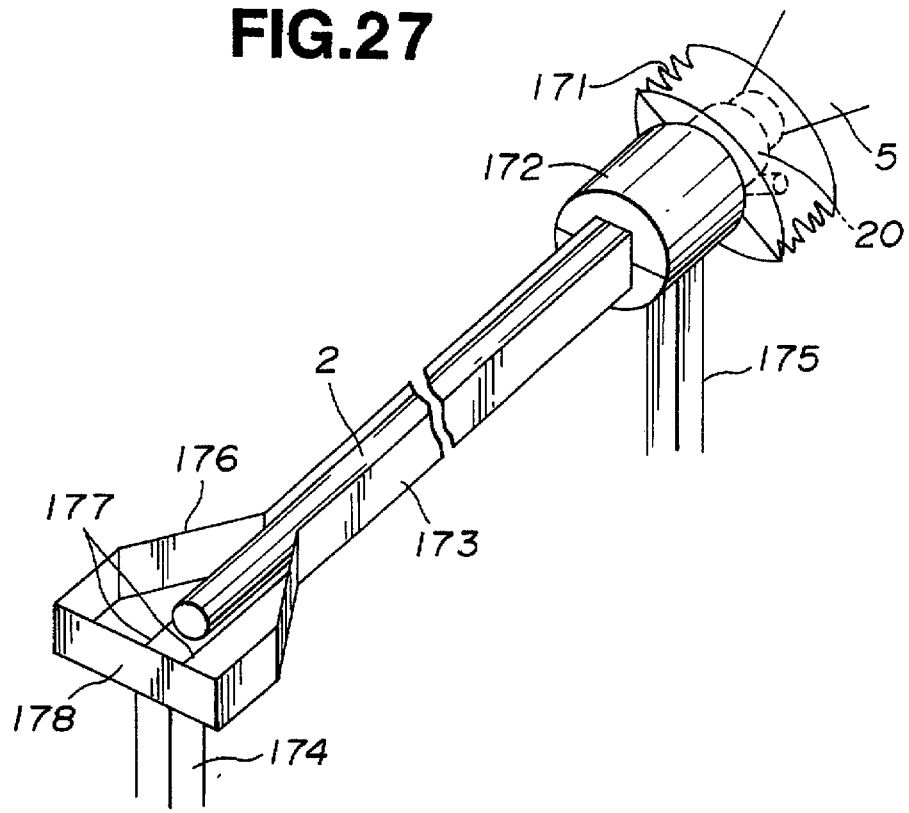
FIG. 27 is a schematic diagram illustrating another structure of a cover holding stage.

In the seventh embodiment described above, the insertion part cover holder 173 of the cover holding stage 170 has a structure such as that shown in FIG. 27. As shown in this figure, the end portion of the insertion part cover holder 173 is spread out into a fan shape thereby forming an insertion end part holder 176. Two frame lines 177 parallel to each other are drawn on the insertion end part holder 176 along the direction in which the insertion part is to be inserted. The distance between two frame lines 177 is set to a value slightly greater than the outer diameter of the cover portion of the endoscope cover 2. The insertion part cover holder 173 is formed such that its cross section has a U shape with a width greater than the output diameter of the endoscope cover 2 so that the insertion part cover holder 173 acts as a guide. At the outermost end portion of the insertion end part holder 176 there is provided a stopper 178 which the endoscope cover 2 will come in contact with when the insertion of the endoscope 3 to be covered makes the endoscope cover 2 move toward the end portion of the insertion end part holder 176.

As a result, the insertion part 31 can be inserted into the endoscope cover 2 without applying too strong force to the endoscope cover 2. Thus, in the final state in which the inlet portion 20 and the operation part 5 are fitted to each other at a proper position, the endoscope cover 2 lies in the form of a straight line within the frame lines as shown in FIG. 27.

Figure 28A:
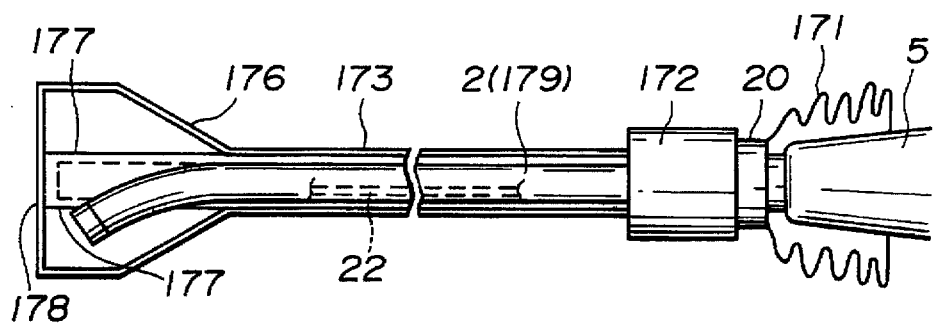
FIG. 28A illustrates a state in which an inlet portion has been raised toward an operation part to a position too high relative to the position of the operation part.
Figure 28B:
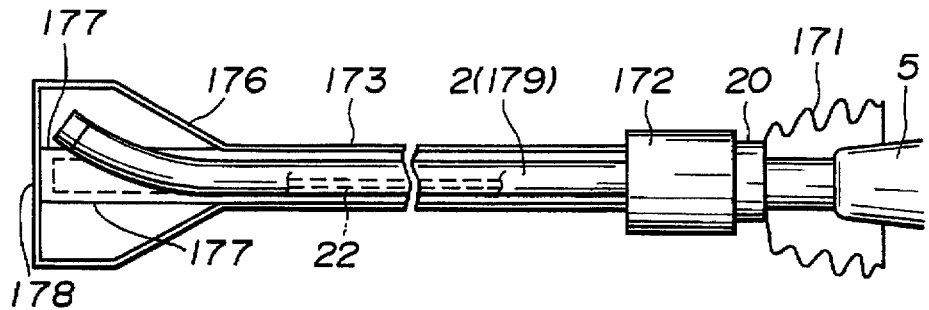
FIG. 28B illustrates a state in which an inlet portion has been pulled back to a position too low relative to the position of an operation part.

However, in the above operation in which the insertion part 31 is inserted into the endoscope cover 2 and the operation part 5 is fitted to the inlet portion 20, if the inlet portion 20 is raised up to a position that is too high relative to the position of the operation part 5, then the sheath 179 forming the endoscope cover 2 is expanded by the insertion part 31 of the endoscope 3 to be covered as shown in FIG. 28A. In such a situation, however, the pipes 22 disposed in the endoscope cover 2 are not so easily expanded as the sheath 179. As a result, the endoscope cover 2 is bent toward the tube side beyond the frame line 177.

Conversely, in the operation in which the insertion part 31 is inserted into the endoscope cover 2 and the operation part 5 is fitted to the inlet portion 20, if the inlet portion 20 is pulled down to a position that is too low relative to the position of the operation part 5, then the insertion part 31 that has been once inserted to the deepest possible position is pulled back. As a result, the sheath 179 is compressed to a length shorter than its natural length. However, since the tubes 22 are not so easily compressed as the sheath, the endoscope cover 2 is bent in the direction opposite to the tubes beyond the frame line 177.

The above phenomenon can be used to check whether or not too strong force is applied to the sheath during the attachment operation. That is, judging from whether the endoscope cover is bent beyond the frame line, it is possible to determine whether or not the operation part is fitted to the inlet portion at a correct position without applying too strong force to the sheath.

Figure 29A:
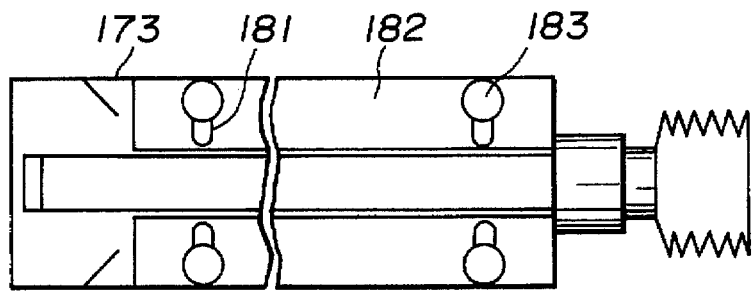
FIG. 29A illustrates a state in which the space between variable guide elements is reduced to the least possible value.
Figure 29B:
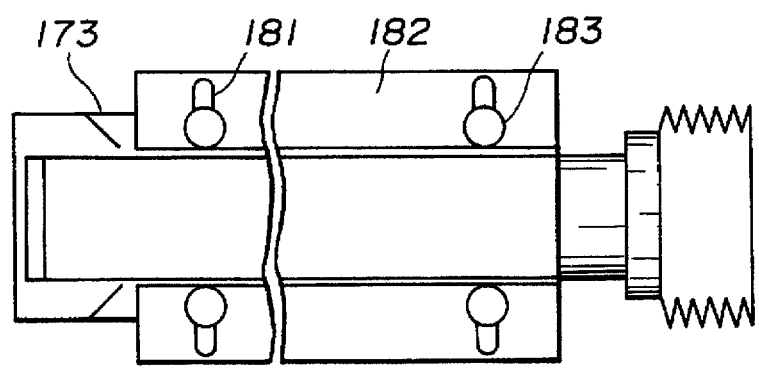
FIG. 29B illustrates a state in which the space between the variable guide elements is expanded to the greatest possible value.

In an alternative embodiment, as shown in FIG. 29A or 29B, there may be provided a variable guide 182 having a plurality of long holes 181 wherein the variable guide 182 is fixed to the insertion part cover holder 173 via the fixing screw 183 so that only one type of cover holding stage can handle various endoscope covers 2 having different diameters. This allows a user having plural types of endoscopes to reduce the cost associated with the endoscope cover attaching apparatus. FIG. 29A illustrates a state in which the distance between the variable guide elements is reduced to the smallest possible value. FIG. 29B illustrates a state in which the distance between the variable guide elements is expanded to the greatest possible value.

Figure 30A:
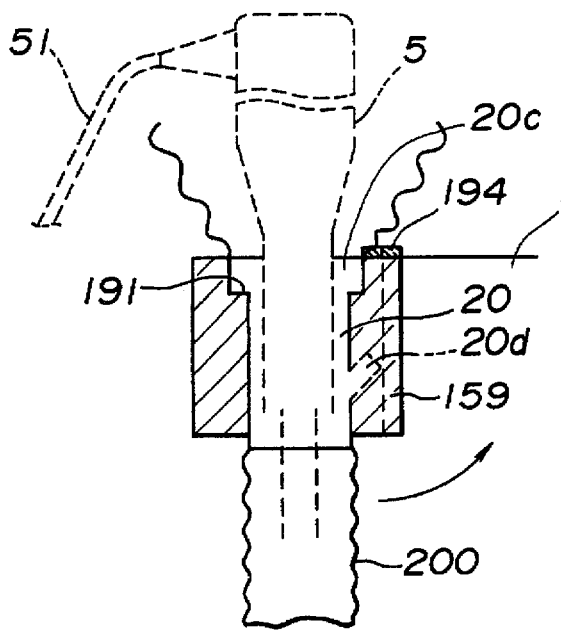
FIG. 30A is a front view illustrating the positional relationship between a first hanger and a rotation stopper.
Figure 30B:
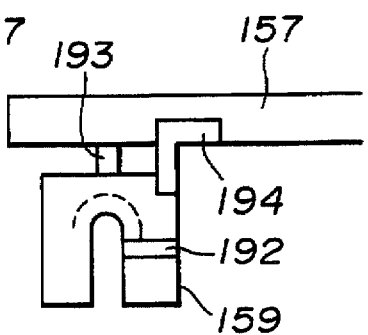
FIG. 30B is a front view illustrating the positional relationship between a first hanger and a rotation stopper.

FIG. 30 is a schematic diagram illustrating another structure of a first hanger.

As shown in FIG. 30, the first hanger 159 has a step 191 for receiving the load applied by a flange 20c disposed in the inlet portion 20, and also has a notch 192 into which the forceps aperture portion 20d of the inlet portion 20 can escape. With this arrangement, the forceps aperture portion 20d is put in the notch 192 and, as a result, it becomes possible to prevent the inlet portion 20 held by the first hanger 159 from rotating in a cross section plane perpendicular to the insertion part direction.

The first hanger 159 is adapted to rotate about the axis 193 disposed on the hanger supporting pipe 155. To control the rotation in the direction represented by the arrow, a rotation stopper 194 is provided on the hanger supporting pipe 157 such that the shoulder portion of the first hanger 159 comes in contact with a part of the rotation stopper 194.

The inlet portion 20 is adapted such that its lower end is connected to the over-tube 200, wherein the first hanger 159 is adapted such that the above connection part is located at the lower end of the first hanger 159 when the inlet portion 20 is attached to the first hanger 150.

When an endoscope cover 2 is attached, the first hanger 159 rotates about the axis 193 in the same direction corresponding to the direction of the cover holding stage 170 in the direction opposite to the rotation stopper. Therefore, this structure never makes it difficult to attach an endoscope cover 2 to an endoscope 3 to be covered. In a situation in which an endoscope 3 to be covered is simply held by the first hanger 159 as shown in FIG. 30A, the endoscope 3 to be covered is pulled toward the universal cord by the weight of the universal cord 51. As a result, the endoscope 3 to be covered comes in contact with the rotation stopper 194 and is held in a vertical position. Thus, except during an attachment operation of an endoscope cover, an endoscope to be covered is held by the first hanger always in a vertical position, which prevents the endoscope from falling down.

Figure 31:
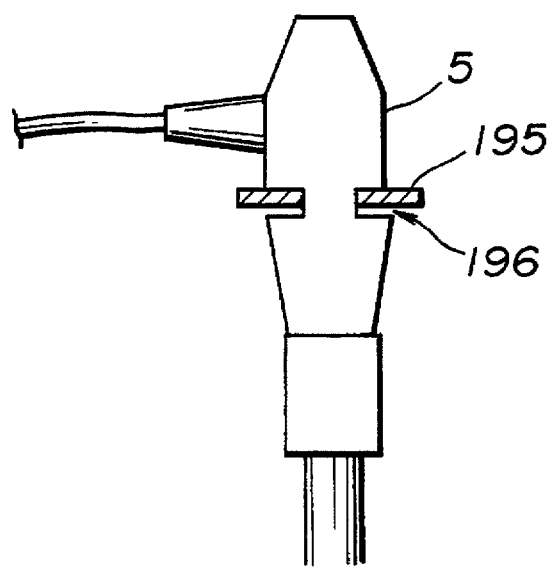
FIG. 31 is a schematic diagram illustrating another structure of a hanger.

Alternatively, as shown in FIG. 31, the hanger unit 195 including the above-described first hanger 158 for holding the operation part 5 of an endoscope to be covered may be arranged such that the hanger unit 195 fits into a fitting grove 196 formed on the operation part 5 thereby holding the operation part 5. This arrangement makes it possible to prevent an endoscope 3 to be covered from slipping out upward when an endoscope cover 2 is attached to the endoscope to be covered 3.

Figure 32:
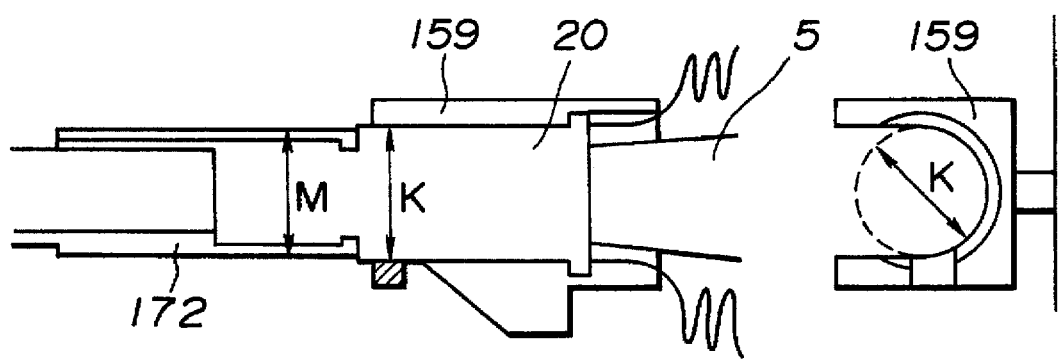
FIG. 32 is a schematic diagram illustrating a modified inlet portion holder of a cover holding stage.

FIG. 32 illustrates an example of a modified inlet portion holder 172 of the cover holding stage 170. In this example, the outer diameter M of the inlet portion holder 172 is set to a value smaller than the inner size K of the first hanger 159. This allows an operator to hang the inlet portion 20 on the first hanger 159 while holding the cover holding stage 170 by a hand. This reduces the number of times that the operator have to touch the inlet portion 20 or the operation part 5 and thus improved cleanness can be obtained.

Referring to FIGS. 33 to 38, daily operation steps associated with the endoscope cover attaching apparatus 1F will be described below for each operation step.

1. Preparatory Procedure prior to Examination

Figure 33A:
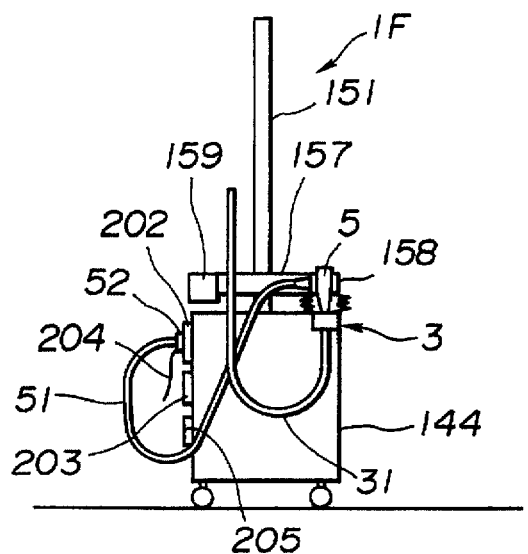
FIG. 33A is a schematic diagram for explanation of an operation step in which an endoscope to be covered is hung on the second hanger.
Figure 33B:
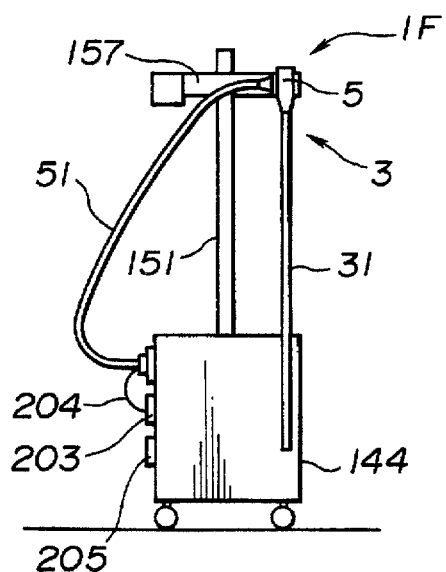
FIG. 33B is a schematic diagram illustrating a situation in which the hanger supporting pipe has been raised up to an upper position of the post.

First, the first hanger 159 and the second hanger 158 of the cover attaching apparatus 1F are disinfected with clean gauze or absorbent cotton containing alcohol. A cleaned endoscope 3 to be covered is then hung on the second hanger 158 as shown in FIG. 33A. The universal cord 51 is connected to the light source 202 via the light source connector 201 disposed at the end of the universal cord 51 extending from the operation part 5 of the endoscope 3 to be covered. In this process, an operator should be careful that the insertion part 31 of the endoscope does not come in contact with a floor. Then, as shown in FIG. 33B, the hanger supporting pipe 157 is raised up to an upper position of the post 151, taking enough care that the insertion part 31 of the endoscope 3 does not touch the floor.

An electric cable 204 is then connected to the video system center 203 via a connector. An air tube, water tube, and suction tube (not shown, hereafter these tubes will be referred to as AWS tubes) are connected to the air, water, and suction unit 205. Then, excessive portions of the AWS tubes are wound around the hook disposed on the cart 144 so that they do not touch the floor.

Figure 33C:
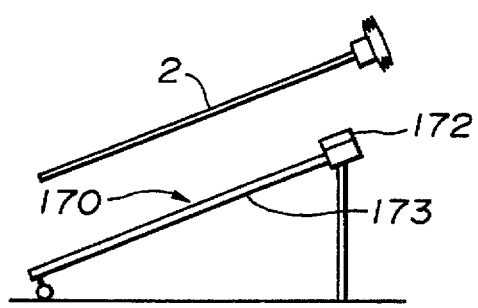
FIG. 33C is a schematic diagram illustrating the cover holding stage in a situation prior to an examination.
Figures 36A, 36B, 36C:
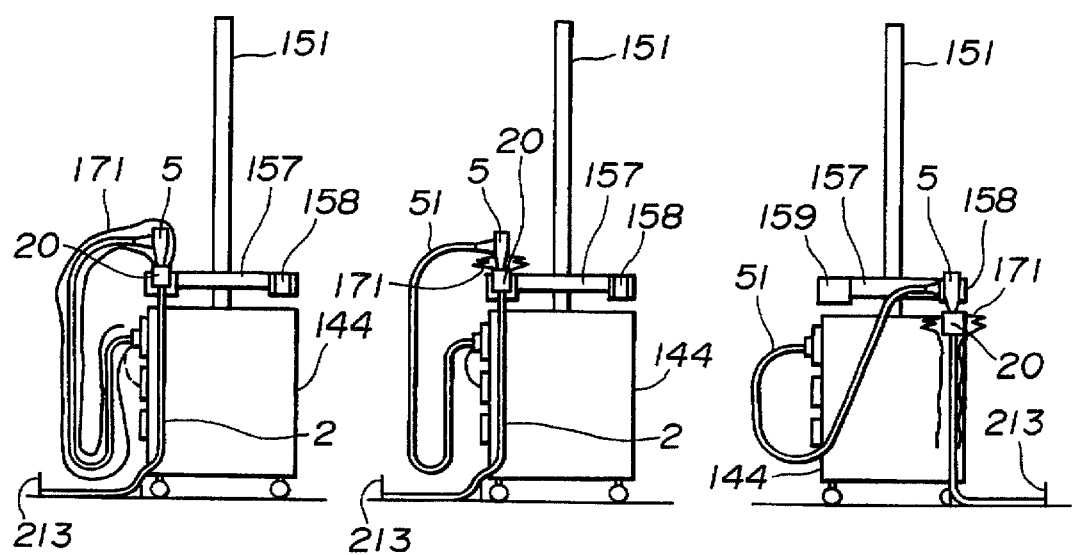
FIG. 36A is a schematic diagram illustrating a situation in which the insertion part of a covered-type endoscope that has been used is put on a tray.
FIG. 36B is a schematic diagram for explanation of an operation step of removing the universal cord cover from the universal cord connected to the endoscope.
FIG. 36C is a schematic diagram for explanation of an operation step of removing the universal cord cover from the endoscope that has been moved to the second hanger.

The inlet portion holder 172 and the insertion part cover holder 173 of the cover holding stage 170 are disinfected using clean gauze or absorbent cotton containing alcohol, as shown in FIG. 33C. A tray 213, which will be described in more detail later in connection with FIG. 36A, is prepared on a shelf of the cart 144.

2. Procedure of Removing a Cover

At the first step of cover attachment, an operator puts on new gloves prior to an attachment operation of an endoscope cover to an endoscope to be covered. An endoscope cover 2 is set on the disinfected cover holding stage 170 shown in FIG. 33C, and placed on the tray 213 covered with a bag and further placed on a vacant space on the shelf of the cart 144.

Figure 34A:
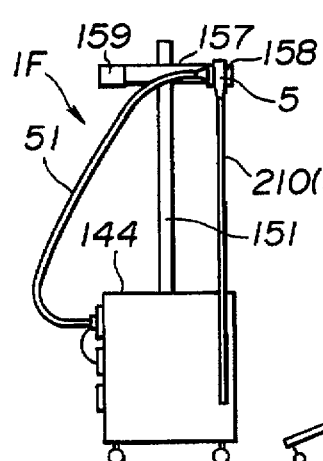
FIG. 34A is a schematic diagram illustrating a situation in which lubricating powder is coated on the surface of the insertion part of an endoscope to be covered.
Figure 34B:
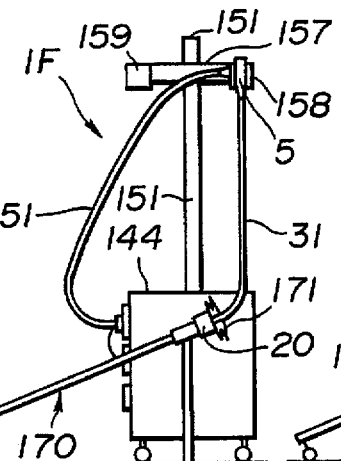
FIG. 34B is a schematic diagram for explanation of an operation step of inserting the insertion part of an endoscope to be covered into an endoscope cover.
Figure 34C:
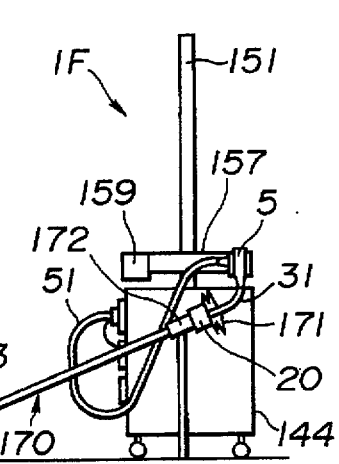
FIG. 34C is a schematic diagram illustrating a situation in which the hanger supporting pipe has been lowered to a lower position of the post.

The surface of the insertion part 31 of the endoscope 3 hung on the second hanger 158 at the upper position is coated with lubricating powder 210 as shown in FIG. 34A. Then, as shown in FIG. 34B, the end portion of the insertion part 31 of the endoscope 3 to be covered which is hung on the second hanger 158 is inserted into the endoscope cover 2 via the inlet aperture formed in the inlet portion 20 of the endoscope cover 2.

When the insertion part 31 of the endoscope to be covered has been inserted into the endoscope cover to a certain extent, the H-pedal is pressed by a foot so as to relieve the lock by which the endoscope 3 to be covered is held at the upper position. The insertion part 31 is then pulled down and the hanger supporting pipe 157 is fixed to the post 151 at a lower position.

Figure 34D:
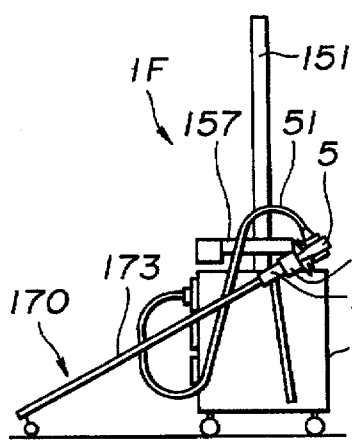
FIG. 34D is a schematic diagram for explanation of an operation step of fitting the operation part to the inlet portion.

At this stage, as shown in FIG. 34D, the inlet portion holder 172 is held by a hand and the remaining insertion part 31 is inserted into the endoscope cover. Then, the operation part 5 is fitted to the inlet portion 20. In this step, if the hard end portion of the endoscope 3 to be covered is not fitted well into the end portion cover of the endoscope cover 2, the hard end portion is fitted into the end portion cover by a manual operation. The operation part 5 is fitted to the inlet portion 20 at a proper position such that the endoscope cover 2 is not bent beyond the frame lines 177, as described earlier referring to FIG. 27.

Figure 34E:
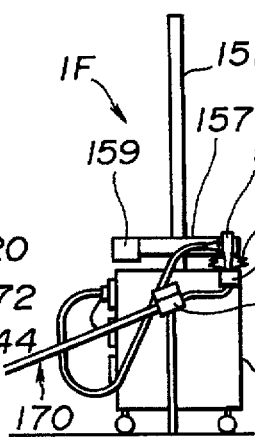
FIG. 34E is a schematic diagram for explanation of an operation step of removing the inlet portion held by the cover holding stage from the cover holding stage.
Figure 34F:
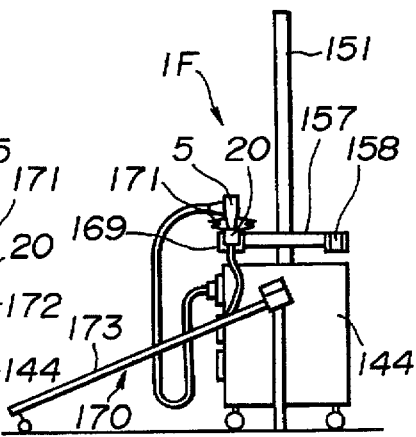
FIG. 34F is a schematic diagram for explanation of an operation step of hanging the endoscope fitted at the inlet portion on the first hanger.
Figure 34G:
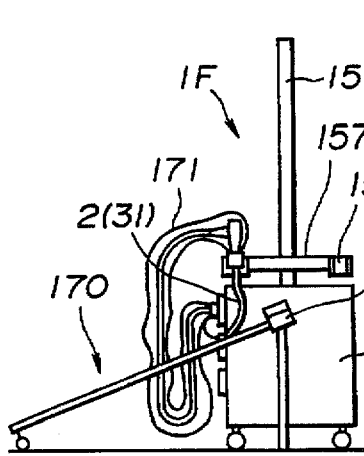
FIG. 34G is a schematic diagram for explanation of an operation step of putting a universal cord cover on the operation part of the endoscope and the universal cord.

Then, the first hanger 159 is covered with a hanger cover having a size slightly greater than the first hanger 159. The inlet portion 20 is removed from the inlet portion holder 172 of the cover holding stage 170 as shown in FIG. 34E. In this operation, the inlet portion holder 172 is moved down while keeping the insertion part 31 of the endoscope 3 on the cover holding stage 170. Then, as shown in FIG. 34F, the endoscope 3 is transferred from the second hanger 158 to the first hanger 159 while keeping the insertion part 31 of the endoscope 3 covered with the endoscope cover 2 remaining on the cover holding stage 170. Only when an examination on a day is started, the other ends of the AWS tubes connected to the air, water, and suction unit 205 are connected to the universal cord 51, which is in turn connected to the air tube, water tube, and suction tube, extending from the inlet portion 20. The operation part 5 and the universal cord 51 are then covered with an universal cord cover 171 as shown in FIG. 34G.

Figure 34H:
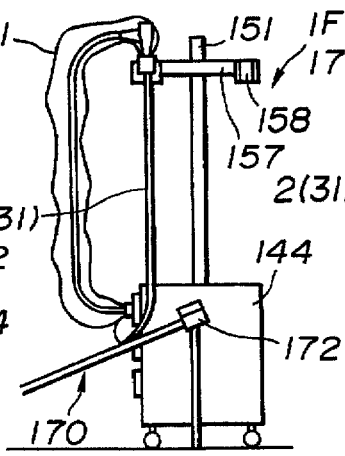
FIG. 34H is a schematic diagram illustrating a situation in which the hanger supporting pipe with the first hanger that holds the endoscope covered with the endoscope cover has been raised to an upper position of the post.
Figure 34I:
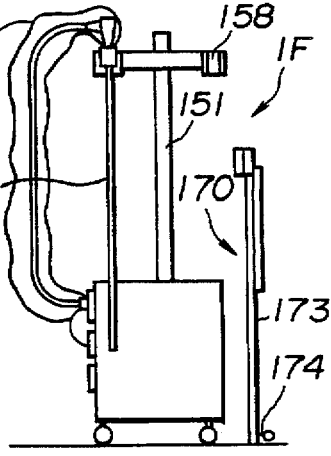
FIG. 34I is a schematic diagram illustrating a situation in which the cover holding stage is in a vertical position.

In this state, a switch unit (not shown) for controlling the air, water, and suction is attached onto the universal cord cover 171, and these cords are connected to the air, water, and suction unit 205. Then, as shown in FIG. 34H, while maintaining the insertion part 31 of the endoscope 3 covered with the endoscope cover 2 remaining on the cover holding stage 170, the L-pedal 165 is pressed by a foot so as to relieve the lock at the lower position and the hanger supporting pipe 157 having the first hanger 159 and the second hanger 158 is raised again up to the upper position and fixed there. The cover holding stage 170 is moved to a proper space and kept there in a state in which the cover holding stage 170 is in a vertical position, as shown in FIG. 34I.

3. Air Tight Test before Actual Use

In a situation shown in FIG. 43I, it is checked whether a pressure tube is connected to the air tight check port of the connector. If yes, then the pressure is applied.

The valve of the pressure tube coupled into the endoscope cover is closed and the endoscope is kept for a predetermined time in this state in which the inside of the endoscope cover is at a high pressure. The value of the pressure gauge disposed in the middle of the path of the pressure tube is visually read. Judging from the change in the pressure read in this way, it is determined whether the endoscope cover is kept in a good air tight condition.

After that, the valve is opened, and the pressure in the endoscope cover is reduced. If it is turned out that there is a hole in the endoscope cover and the endoscope cover is not air tight, then the endoscope cover is removed, and another endoscope cover is attached to the endoscope according to the procedure described above. Then, the air tight test is performed again according to the same procedure so as to check whether the endoscope cover 2 has no holes.

4. Procedure before Examination

In the situation shown in FIG. 34I, the H-pedal 164 is pressed by a foot so as to relieve the lock of the hanger supporting pipe 157 having the first and second hangers 159 and 158 held at the upper position.

Figure 35:
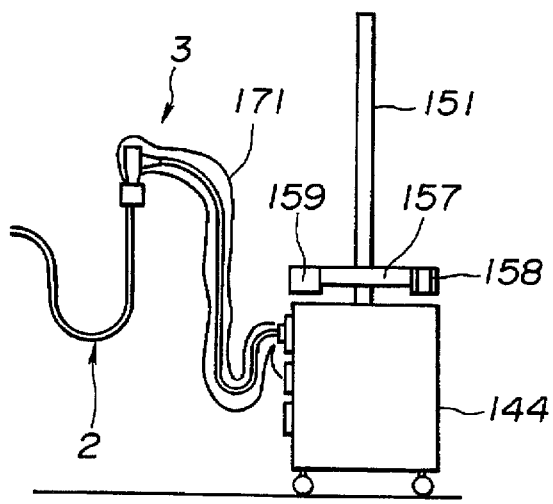

Then, as shown in FIG. 35, the insertion part 31 of the endoscope 3 covered with the endoscope cover 2 is held by a hand, and the hanger supporting pipe 157 having the first and second hangers 159 and 158 is pulled down to a lower position and fixed there, taking care that the insertion part 31 does not touch the floor. In this state, the operation part 5 is removed from the first hanger 159 and used for an examination.

5. Procedure after Examination

First, as shown in FIG. 36A, the tray 213 is placed just below the first hanger 159, and the insertion part 31 is wound into the form of loops on the tray 213. Then, the endoscope 3 covered with the endoscope cover 2 is hung on the first hanger 159 such that the inlet portion 20 is held by the first hanger 159. At this stage, the cord of the switch unit is disconnected from the air, water, and such unit 205, and the switch unit is removed from the operation part 5.

The universal cord cover 171 is removed from the connector position. The universal cord cover 171 is then wound in a bundled form and placed near the inlet portion 20, as shown in FIG. 36B.

Furthermore, the AWS tubes are disconnected from the air, water, and suck tubes. Then, as shown in FIG. 36C, the inlet portion 20 is removed from the first hanger 159, and the operation part 5 is hung on the second hanger 158. As shown in FIGS. 36B and 36C, when the endoscope 3 is transferred from the first hanger 159 to the second hanger 158, the tray 213 is moved from the position just below the first hanger 159 to a position just below the second hanger 158.

The used hanger cover is removed from the first hanger 159 and put on the tray 213. In this operation, as shown in FIG. 36C, the universal cord cover 171 is turned inside out and the insertion part 31 is covered with the turned universal cord cover 171 thereby preventing the contaminated matter from being scattered.

6. Air Tight Test After Examination

First, the L-pedal 165 is pressed by a foot so as to relieve the lock of the hanger supporting pipe 157 at the lower position. Then, as shown in FIG. 37A, the hanger supporting pipe 157 rises up to an upper position, and is fixed there.

Figure 37A:
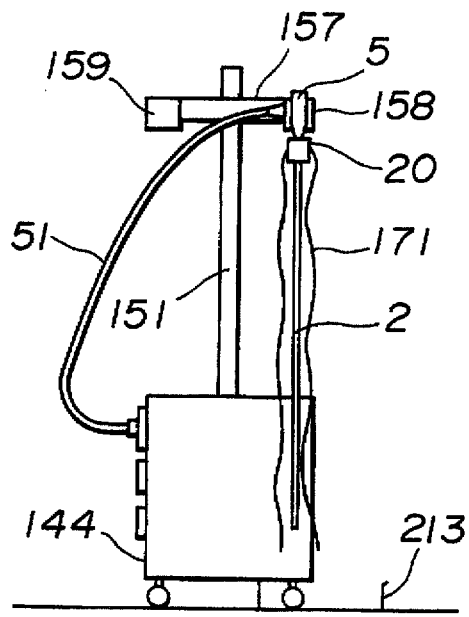
FIG. 37A is a schematic diagram illustrating a situation in which the hanger supporting pipe with the second hanger, that holds the endoscope from which the universal cord cover has been removed, has been raised to an upper position.

In a state shown in FIG. 37A, it is checked whether a pressure tube is connected to the air tight check port of the connector. If yes, then the pressure is applied.

The valve of the pressure tube coupled to the endoscope cover is closed and the endoscope is kept for a predetermined time in this state in which the inside of the endoscope cover is at a high pressure. The value of the pressure gauge disposed in the middle of the path of the pressure tube is visually read. Judging from the change in the pressure read in this way, it is determined whether the endoscope cover is kept in a good air tight condition. After that, the valve is opened, and the pressure in the endoscope cover is reduced.

If the air tight test reveals that the endoscope cover has a hole, then the endoscope cover is removed from the endoscope and the endoscope is cleaned. If it is concluded that the endoscope cover has no hole, the endoscope is covered with a new endoscope cover for further use in examination.

Figure 37B:
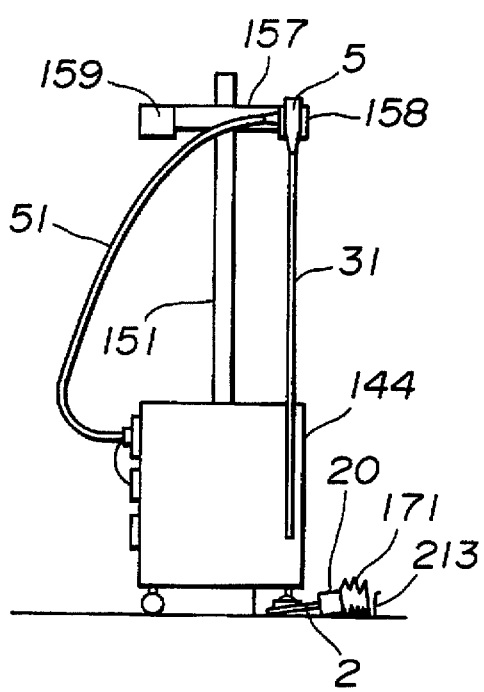
FIG. 37B is a schematic diagram illustrating a situation in which the endoscope cover has been removed from the insertion part of the endoscope.

The end portion cover is removed from the hard end part of the endoscope, and the fitting between the operation part 5 and the inlet portion 20 is relived as shown in FIG. 37B. The endoscope cover 2 is held by a hand via the turned universal cord cover, and the pulled down so as to remove it. The removed the endoscope cover 2 is disposed of on the tray 213. The used gloves are also disposed of on the tray 213. The endoscope cover, gloves, and hanger cover are packed by the bag put on the tray 213, and all are disposed of. An operator should do the above operation taking enough care that his/her hand and other body portion are not contaminated.

7. Procedure at the End of a Day

Figure 38A:
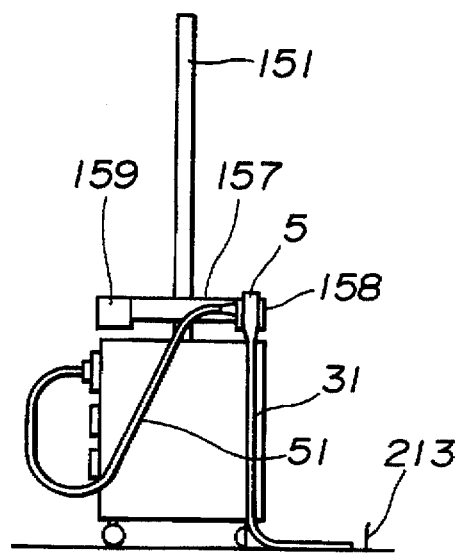
FIG. 38A is a schematic diagram illustrating a situation in which the hanger supporting pipe with the second hanger that holds the endoscope has been lowered to a lower position.

To take back, maintain, and keep tools, the insertion part 31 of the endoscope 3, that is held by the second hanger 158 at the upper position as shown in FIG. 37B, is pulled down, and the H-pedal 164 is pressed by a foot so as to move down the first hanger 159 and the second hanger 158 to a lower position. Thus, the first and second hangers 159 and 158 are fixed at the lower position as shown in FIG. 38A. The insertion part 31 is put on the tray 213 on which no bag is placed.

The AWS tubes are disconnected, and hung on the hook disposed on the cart 144. The tube and cable are disconnected from the air tight check port of the connector, and the connector 52 is removed from the light source 202.

Figure 38B:
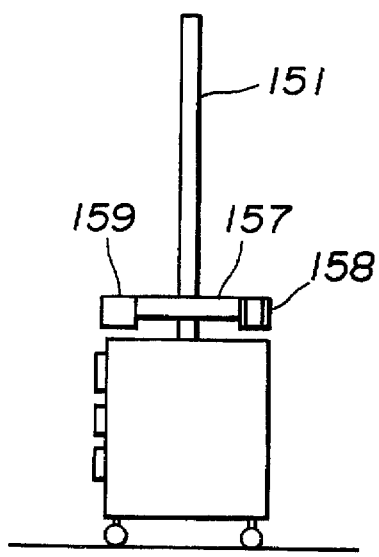
FIG. 38B is a schematic diagram illustrating a situation in which all procedures have been completed at the end of a day.

Then, as shown in FIG. 38B, the endoscope 3 is removed from the second hanger 158. The endoscope 3 is then cleaned and disinfected, and kept at a predetermined place. The tray 213 is also cleaned and disinfected, and kept at a proper place. The AWS tubes are disconnected from the air, water, and suction unit 205, and disposed of.

Finally, the inlet portion holder 172 of the cover holding stage 170, and the cover holder 39 are cleaned with clean gauze or absorbent cotton containing alcohol. The cleaned cover holding state 170 are kept at a proper place. The first hanger 159 and the second hanger 158 are also cleaned with clean gauze or absorbent cotton containing alcohol.

In conventional covered-type endoscopes, it is impossible to pull up an endoscope cover from a predetermined position further toward the operation part. As a result, although the inlet portion has come in contact with the operation part, the end portion of the endoscope cover does not come in contact with end portion of the endoscope. This causes degradation in attachment quality as well as view field quality. Thus, there is a need for a covered-type endoscope that provides high quality attachment between an endoscope and an endoscope cover. To avoid the above problem, the present invention provides a connection structure between the inlet portion 21 of an endoscope cover 2 and the operation part 5 of an endoscope 3 which will be described in detail below.

Figure 39:
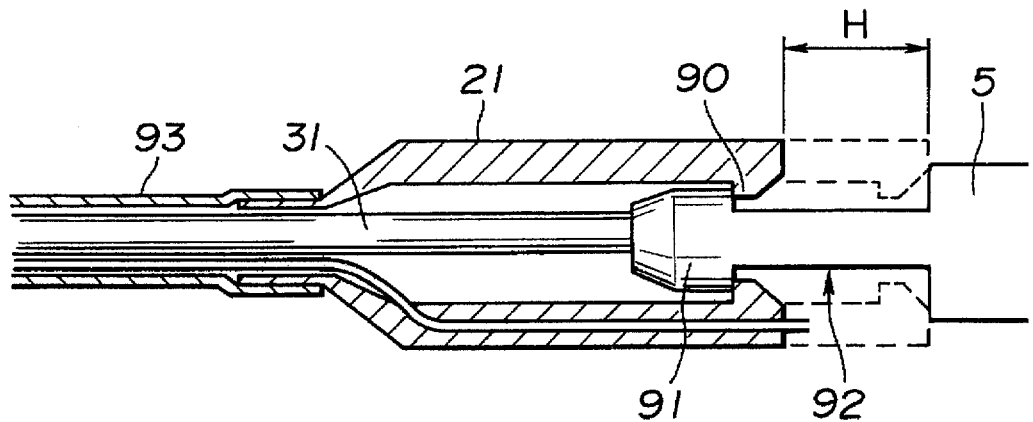
FIG. 39 is a schematic diagram illustrating a method of connecting the operation part to the inlet portion.

As shown in FIG. 39, the inlet portion 21 of an endoscope cover 2 is made up of an elastic material in such a manner that a raised portion 90 is formed on the inlet portion 21 near the operation part. On the other hand, a groove 92 is formed on the projection 91 extending from the operation part 5. The raised portion 90 is formed in such a manner that the inner diameter of the raised portion 90 is smaller than the outer diameter of the end portion of the projection 91, and at the same time the inner diameter of the raised portion 90 is greater than the outer diameter of the groove 92. The projection 91 is formed in a thin and long shape wherein it is long in the axial direction. Taking into account the expanding length of the sheath 93 that occurs during an attachment operation of an endoscope, the width of the groove 92 of the projection 91 is determined such that the inlet portion 21 can move for example distance H.

the end face of the raised portion 90 near the operation part as well as the end portion of the projection 91 is beveled so that the raised portion 90 and the projection 91 can be easily fitted to each other and can also separated easily from each other.

With this arrangement, if the inlet portion 21 is pressed toward the operation part 5, the raised portion 90 goes over the end portion of the projection 91 and falls down into the groove 92. However, in a state in which the raised portion 90 of the inlet portion 21 simply gets into the groove 92, the sheath 93 is in an expanded state, and, as a result, the end of the endoscope cover 2 has no contact to the end of the endoscope 3. To solve the above problem, the inlet portion 21 is moved toward the operation part by an amount corresponding to the stroke H formed in the groove 92 of the projection 91. As a result, the sheath 93 is pulled up, and thus the end of the endoscope cover 2 comes in contact with the end of the endoscope 3, and then the raised portion 90 is moved back toward the end position so that the sheath 93 comes to have its natural length. Thus, the attachment is complete.

In this structure, as described above, the inlet portion is adapted to move in the groove of the operation part so as to expand the sheath until the end of the endoscope cover reaches the end of the of endoscope. As a result, it is possible to prevent a problem associated with the view field.

Figure 40A:
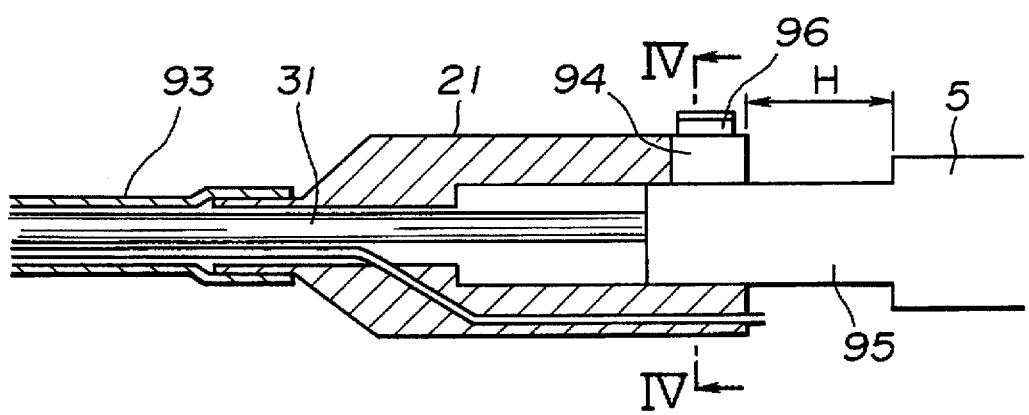
FIG. 40A is a transverse sectional view illustrating a general structure of a connecting portion.
Figure 40B:
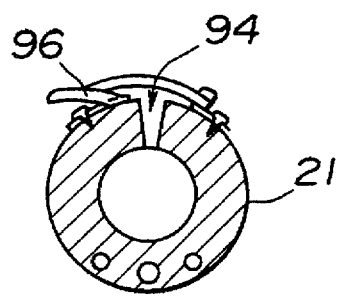
FIG. 40B is a cross-sectional view taken along the line IV—IV of FIG. 40A.

Alternatively, as shown in FIGS. 40A and 40B, an inlet portion 21 may also be made up of an elastic material in such a manner that a notch 94 is formed in the end portion of the inlet portion 21 so that the inlet portion 21 can be fixed at an arbitrary position to the cylindrical portion 95 projecting from the operation part 5.

In this technique, the inlet portion 21 is adapted to have an inner diameter slightly greater than the outer diameter of the cylindrical portion 95 of the operation part 5. Furthermore, the cylindrical portion 95 is adapted to have a stroke H. In an attachment operation, the inlet portion 21 is moved once toward the operation part by an amount equal to the stroke H so as to expand the sheath 93 so that the end of the endoscope cover 2 comes in contact with the end of the endoscope 3. After that, the inlet portion 21 is fixed at a proper arbitrary position with a fixing mechanism 96. This provides similar functions to those obtained in the previous example.

Figure 41:
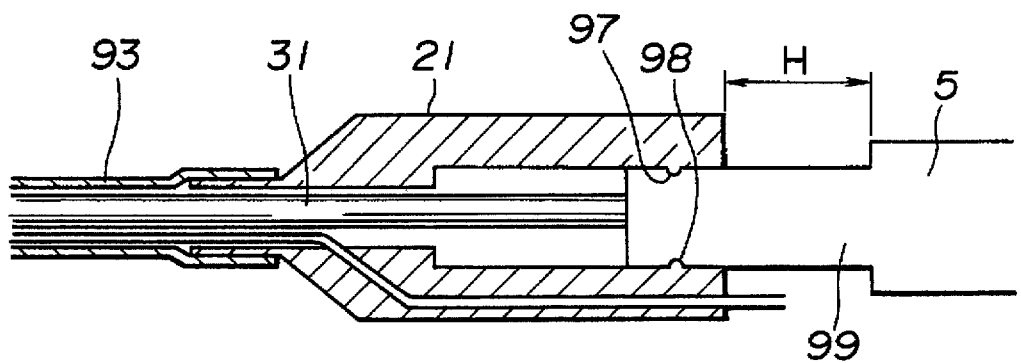
FIG. 41 is a schematic diagram illustrating still another method of connecting the operation part to the inlet portion.

In still another alternative, as shown in FIG. 41 a raised portion 97 is formed on the inner wall of the inlet portion 21, and a groove 98 is formed on the operation part 5 such that the raised portion 97 can fit into the groove 98. Furthermore, a cylindrical portion 99 is formed such that a stroke H can be obtained. The raised portion 97 of the inlet portion 21 is moved once beyond the groove 98 by an amount corresponding to the stroke H thereby expanding the sheath until the end of the endoscope cover 2 comes in contact with the end of the endoscope 3. After that, the raised portion 97 of the inlet portion 21 is moved back to the groove 98 at which the raised portion 97 is fitted into the groove 98, which can be recognized by an operator via clicking. Thus, reliable connection between the inlet portion 21 and the operation part 5 can be achieved.

Figure 42:
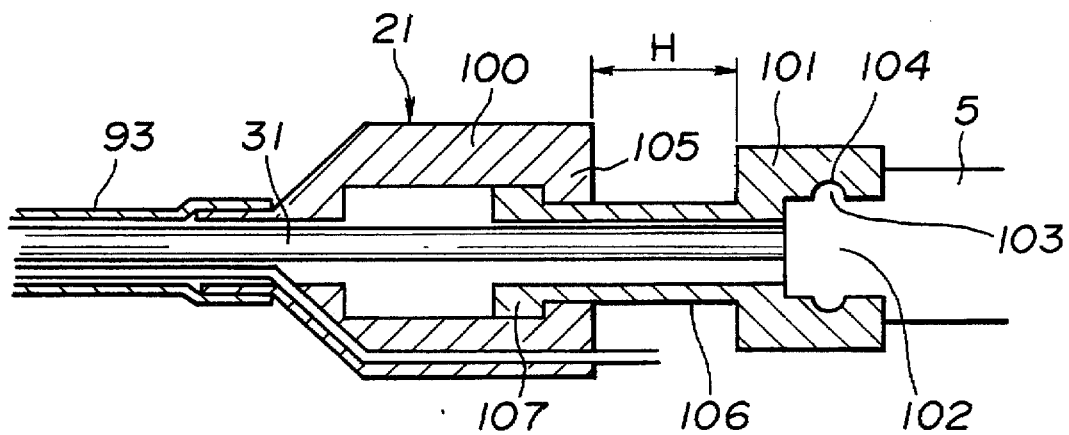
FIG. 42 is a schematic diagram illustrating another method of connecting the operation part to the inlet portion.

FIG. 42 illustrates another alternative, in which the inlet portion 21 is composed of a sliding portion 100 and a fixed portion 101, wherein the fixed portion 101 is made up of an elastic material such that it can be connected to the connecting portion 102 formed on the operation part 5. This connection portion 102 has a clicking extrusion 103 which can be fitted into a clicking groove 104 formed on the inner wall of one end of the fixed portion 101 whereby the operation part 5 and the inlet portion 21 can be connected and disconnected freely. A raised portion 105 is formed at the end portion of the sliding portion 100 near the operation part such that the raised portion 105 can slide freely in the axial direction across the sliding face 106 formed on the fixed portion 101. A stopper flange 107 is formed at the other end of the fixed portion 101 so as to prevent the fixed portion 101 from slipping out of the sliding portion 100. The length of the sliding face 106 is set to such a value that the sliding portion can slide by an amount equal to the stroke H.

With this arrangement, the clicking extrusion 103 formed on the operation part 5 is fitted into the clicking groove 104 of the fixed portion 100 of the inlet portion 21 thereby connecting the inlet portion 21 to the operation part 5. The sliding portion 101 is moved by an amount equal to the stroke H so as to expand the sheath 93 such that the end of the endoscope cover 2 comes in contact with the end of the endoscope 3. Thus, the attachment operation is complete. s One know technique to more easily perform an attachment operation is to expand the endoscope cover by supplying air into the endoscope cover thereby increasing the clearance between an endoscope cover and the insertion portion of an endoscope to be covered. However, in conventional covered-type endoscope, an inflation port is formed in the inlet portion and dust or lubricating powder used to improve the slipping characteristic between the endoscope cover and the endoscope to be covered accumulates on the inner wall at the end portion of the endoscope cover. The dust or the lubricating power further sticks to an objective lens or illumination lens of the endoscope or sticks to the inner face of a lens cover provided at the end portion of the endoscope cover, which results in degradation in the quality regarding the view field. Therefore, there is a need for a covered-type endoscope that can provide high quality view field.

Figure 43:
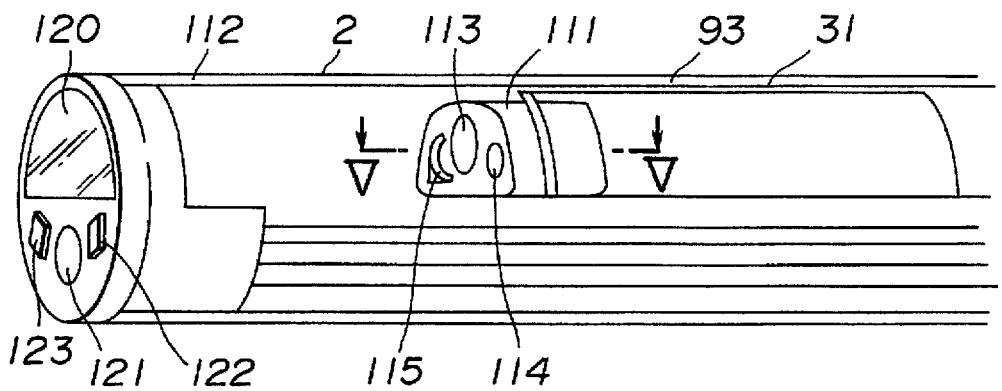
FIG. 43 is a schematic diagram illustrating a covered-type endoscope in a state in which an endoscope cover is attached to an endoscope.
Figure 44:
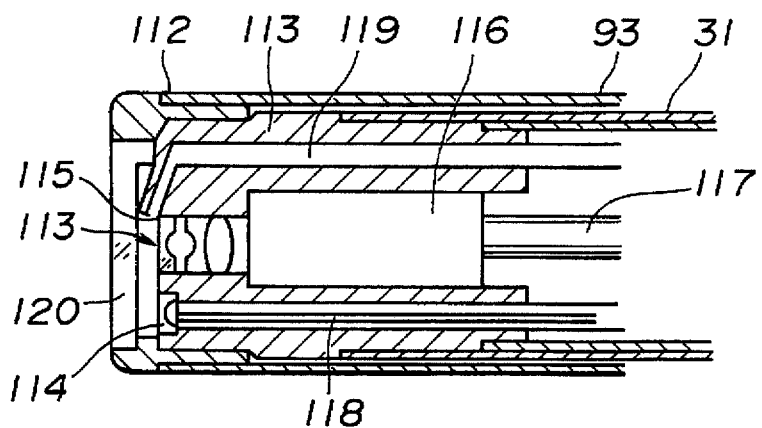
FIG. 44 is a transverse sectional view illustrating a covered-type endoscope.
Figure 45:
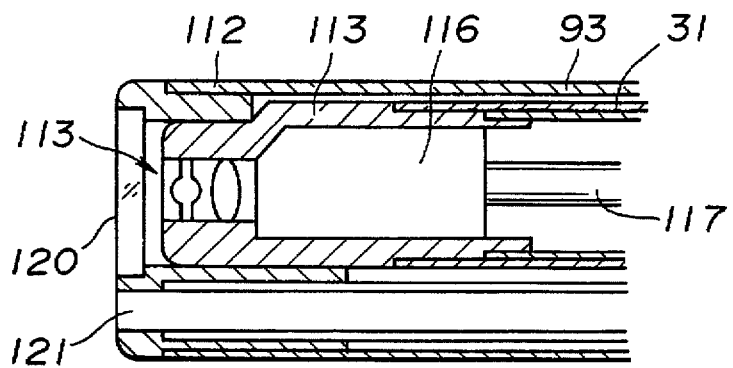
FIG. 45 is a longitudinal sectional view illustrating a covered-type endoscope.

This requirement can be achieved by the embodiment described below referring to FIGS. 43 to 45. As shown in these figures, a hard end portion 111 is formed at the end of the insertion part 31, and an end portion cover 112 is formed at the end of the endoscope cover 2 such that the hard end portion 111 can be fitted into the end portion cover 112.

The hard end portion 111 has, on its end face, an objective optical lens 113, an illumination optical lens 114, and an inflation nozzle 115. The objective optical lens 113 is coupled to an image sensing unit 116 which is in turn connected to a signal cable 117. The illumination optical lens 114 is coupled to an illumination optical fiber 118. The inflation nozzle 115 is connected to an inflation tube 119.

The end portion cover 112 has a lens cover 120, an operation tool through-hole 121, an air nozzle 122, and a water nozzle 123.

In an attachment operation of an endoscope cover, air is supplied via the inflation tube 119 and is injected through the inflation nozzle 115. As a result, the sheath 93 is expanded, and thus the clearance between the insertion part 31 and the sheath 93 is increased.

The inflation nozzle 115 is disposed such that it points to the objective optical lens 113 and the illumination optical lens 114 and thus lubricating powder such as corn starch powder or talc powder coated on the inner wall of the sheath 93, or dust adhering to the objective optical lens 113 or the illumination optical lens can be blown off. Similarly, powder or dust adhering to the inner face of the lens cover 120 is also blown off.

With this arrangement, as described above, it becomes easier to perform attachment operation owing to the inflation effect. Furthermore, power or dust adhering to the optical system is blown off and thus clear view field can be obtained.

Figure 46A:
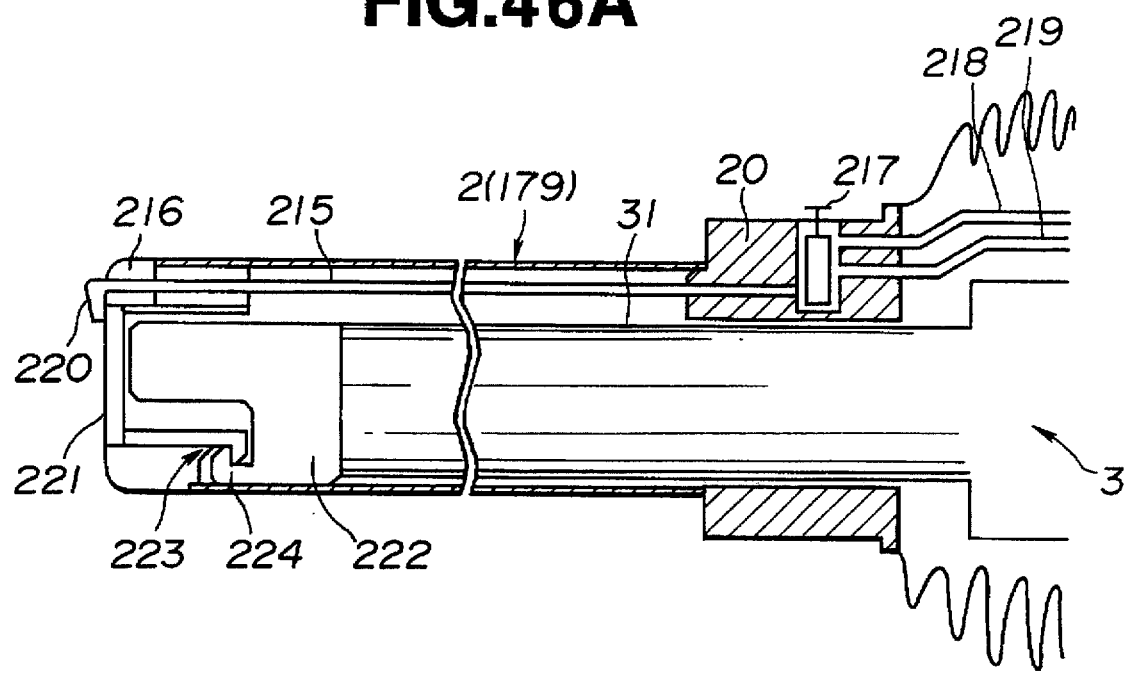
FIG. 46A is a schematic diagram illustrating a structure of a tube and a state in which an endoscope is fitted to an endoscope cover.

The structure is formed by cutting out a part of the hard end portion 111, and thus the insertion part becomes thinner, which makes it easier to insert the insertion part into a body cavity. FIG. 46 illustrates another embodiment in which there are shown a tube of an endoscope cover 2, an endoscope cover 2, and an endoscope 3 to be covered. As shown in FIG. 46A, the endoscope cover 2 has an air and water tube 215 for supplying air and water. In this structure, there is only one tube extending from the inlet portion 20 to the end portion cover 216, and both air and water are supplied through this tube. Inside the inlet portion 20, there is provided a switching valve 217 for switching the supplying mode among air, water, and injection modes. This switching valve 217 is connected to the air and water tube 215. The switching valve 217 is also connected to a water tube 218 and an air tube 219. In this arrangement, only one tube 215 is required for supplying both air and water, and thus it becomes possible to make the diameter of the insertion part smaller.

A nozzle 220 is formed in the end portion cover 216, wherein the nozzle is connected to the air and water tube 15. A lens cover 221 is disposed at a position the aperture of the nozzle 220 points to, wherein a water repellent material is coated on the lens cover 221.

Furthermore, a hard end portion 222 is disposed at the end of the insertion part 31 of the endoscope 3. A stopper 223 is formed on the end portion cover 216 in such a manner that it has an aperture extending in the radial direction. On the other hand, a fitting portion 224 is formed on the hard end portion 222 such that the stopper fits to the fitting portion 224. The combination of the stopper 223 and the fitting portion 224 prevents the fitting portion from being separated owing to the sheath 179.

Figure 46B:
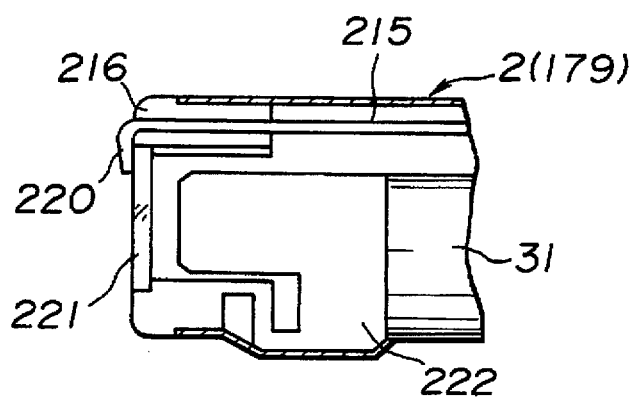
FIG. 46B is a schematic diagram illustrating a state in which the fitting between the endoscope and the endoscope cover has been relieved.

When the hard end portion 222 is removed from the end portion cover 216, the fitting portion 224 of the hard end portion 222 is moved toward the aperture of the stopper 223 of the end portion cover 216, as shown in FIG. 46B. Thus, the hard end portion 222 moves against the clamping force applied by the sheath and the fitting between the stopper 223 and the fitting portion 224 is relived. The hard end portion 222 is moved toward the hand operation position, and removed from the other portion. This structure makes it easier to attach and remove the hard end portion 222 to or from the end portion cover 216, while it does not easily slip out when used.

Although the invention has been described above with reference to specific embodiments, those with skill in the art will readily recognize that various modifications and changes may be made without departing from the spirit and scope of the invention. It is to be understood that the invention is not limited to these specific embodiments except as defined in the appended claims.

What is claimed is:

1. A combination of an endoscope, an endoscope cover and an endoscope cover attaching apparatus, comprising:
a cover holding stage for holding an endoscope cover in a straight line, said endoscope cover including an insertion part cover for covering an insertion part of said endoscope, and an insertion part inlet aperture located at an end of said insertion part cover near a hand operation position, wherein a tube is disposed in said endoscope cover;
an operation part holding stage for holding an operation part of said endoscope, said endoscope including said insertion part in which an observation optical system is disposed, and said operation part which also serves as a grip of said endoscope;

rotation means for adjusting a rotational position of said operation part of said endoscope relative to a rotational position of said insertion part inlet aperture of said endoscope cover, wherein said rotation means is disposed on at least one of said operation part holding stage and said cover holding stage; and
wherein said cover holding stage is slanted at an angle greater than 90° relative to a vertical direction, in such a manner that said insertion part does not come to a position higher than said operation part.

2. The combination of said endoscope, said endoscope cover and said endoscope cover attaching apparatus, according to claim 1, wherein said operation part of said endoscope to be covered is held in parallel to said operation part holding stage forming an operation part holder.

3. The combination of said endoscope, said endoscope cover and said endoscope cover attaching apparatus, according to claim 1 or 2, wherein said rotation means is adapted to rotate at least said operation part fixed to said operation part holding stage, in such a manner that rotation of said operation part occurs in a plane substantially perpendicular to an longitudinal axis of said insertion part of said endoscope to be covered.

4. The combination of said endoscope, said endoscope cover and said endoscope cover attaching apparatus, according to claim 3, wherein said endoscope cover and said endoscope are moved in a direction to face each other, thereby attaching said endoscope cover to said endoscope.

5. The combination of said endoscope, said endoscope cover and said endoscope cover attaching apparatus, according to claim 1, wherein said rotation means is adapted to rotate said endoscope cover fixed to said cover holding stage, in such a manner that rotation of said endoscope cover occurs in a plane substantially perpendicular to said longitudinal axis of said insertion part of said endoscope to be covered.

6. The combination of said endoscope, said endoscope cover and said endoscope cover attaching apparatus, according to claim 5, wherein said endoscope to be covered is attached to said endoscope cover which is kept on said cover holding stage.

7. The combination of said endoscope, said endoscope cover and said endoscope cover attaching apparatus, according to claim 5, wherein said endoscope cover is fixed to said cover holding stage.

8. The combination of said endoscope, said endoscope cover and said endoscope cover attaching apparatus, according to claim 1, wherein said cover holding stage has a semi-circular shaped cross section.

9. The combination of said endoscope, said endoscope cover and said endoscope cover attaching apparatus, according to claim 1, wherein said cover holding stage has a V-shaped cross section.

10. The combination of said endoscope, said endoscope cover and said endoscope cover attaching apparatus, according to claim 1, wherein said cover holding stage has a U-shaped cross section.

11. The combination of said endoscope, said endoscope cover and said endoscope cover attaching apparatus, according to claim 1, wherein said cover holding stage and said operation part holding stage are adapted to be covered with a disinfected sheet.

12. The combination of said endoscope, said endoscope cover and said endoscope cover attaching apparatus, according to claim 1, wherein a space is provided between said cover holding stage and said operation part holding stage.

13. The combination of said endoscope, said endoscope cover and said endoscope cover attaching apparatus, according to claim 1, wherein a connector holder means for holding a connector of said endoscope to be covered is disposed at a side of said cover holding stage.

14. The combination of said endoscope, said endoscope cover and said endoscope cover attaching apparatus, according to claim 13, wherein an arm capable of being expanded and contracted freely is provided on said operation part holding stage.

15. The combination of said endoscope, said endoscope cover and said endoscope cover attaching apparatus, according to claim 1, further including fixing means for fixing an end portion of said endoscope cover to said endoscope cover holding stage.

16. The combination of said endoscope, said endoscope cover and said endoscope cover attaching apparatus, according to claim 15, wherein a plurality of said fixing means are provided so as to handle various types of said endoscope cover, each various type of said endoscope cover having different lengths.

17. The combination of said endoscope, said endoscope cover and said endoscope cover attaching apparatus, according to claim 1, wherein at a connecting portion between an inlet portion of said endoscope cover and said operation part of said endoscope to be covered, a stopper means, is provided, for stopping said inlet portion and a moving space in which said inlet portion moves from said stopper means toward said operation part.

18. The combination of said endoscope, said endoscope cover and said endoscope cover attaching apparatus, according to claim 1, wherein an inflation tube is disposed in said insertion part of said endoscope to be covered wherein said inflation tube is connected to a nozzle formed at a hard end portion of said insertion part.

19. A combination of an endoscope, a endoscope cover and an endoscope cover attaching apparatus, comprising:
   an operation part holding stage having means for holding an operation part of said endoscope at a variable angle between a longitudinal axis of said operation part and a vertical direction, said endoscope including an insertion part in which an observation optical system is disposed, and said operation part which also serves as a grip of said endoscope; and
   a cover holding stage having means for holding said endoscope cover at a variable angle between a longitudinal axis of said endoscope cover and said vertical direction, said endoscope cover including an insertion part cover means for covering an insertion part of said endoscope, and an insertion part inlet aperture located at an end of said insertion part cover means near a hand operation position, wherein a tube is disposed in said endoscope cover.

20. The combination of said endoscope, said endoscope cover and said endoscope cover attaching apparatus, according to claim 19, wherein a connector holder means for holding a connector of said endoscope to be covered is disposed at a side of said operation part holding stage.

21. The combination of said endoscope, said endoscope cover and said endoscope cover attaching apparatus, according to claim 19, wherein said endoscope to be covered is attached to said endoscope cover so that a connector of said endoscope is connected to a light source.

22. The combination of said endoscope, said endoscope cover and said endoscope cover attaching apparatus, according to claim 19, wherein said operation part holding stage for holding said endoscope is formed as an integral part of a cart on which an endoscope system, including a light source and a video processor, is placed.

23. The combination of said endoscope, said endoscope cover and said endoscope cover attaching apparatus, according to claim 19, wherein said cover holding stage is rotated from a position at a 90° angle relative to said vertical direction thereby attaching said endoscope cover to said endoscope, wherein a height of said operation part of said endoscope to be covered is kept unchanged, and said height of said insertion part is kept lower than said height of said operation part.

24. The combination of said endoscope, said endoscope cover and said endoscope cover attaching apparatus, according to claim 19 or 23, wherein said cover holding stage can be in a vertical position in which an end portion of said insertion part of said endoscope cover faces down.

25. The combination of said endoscope, said endoscope cover and said endoscope cover attaching apparatus, according to claim 19, wherein said operation part holding stage and said cover holding stage are moved by means for rotating thereby attaching said endoscope cover to said endoscope to be covered.

26. The combination of said endoscope, said endoscope cover and said endoscope cover attaching apparatus, according to claim 19, wherein said operation part of said endoscope held by said operation part holding stage is moved downward and also moved by means for rotating thereby attaching said endoscope cover to said endoscope to be covered.

27. The combination of said endoscope, said endoscope cover and said endoscope cover attaching apparatus, according to claim 25 or 26, wherein said operation holding stage for holding said operation part is rotated by said rotating means which includes a rack and pinion.

28. The combination of said endoscope, said endoscope cover and said endoscope cover attaching apparatus, according to claim 25 or 26, wherein said operation holding stage for holding said operation part is fixed in a free fit fashion so that said operation holding stage can rotate freely.

29. The combination of said endoscope, said endoscope cover and said endoscope cover attaching apparatus, according to claim 25 or 26, wherein a fixing tool of said operation holding stage for fixing said operation part has a width greater than a width of said operation part.

30. The combination of said endoscope, said endoscope cover and said endoscope cover attaching apparatus, according to claim 19, wherein said operation part of said endoscope held by said operation part holding stage is moved by means for rotating, and said cover holding stage is moved by means for rotating from an initial state to a vertical position thereby attaching said endoscope cover to said endoscope to be covered.

31. The combination of said endoscope, said endoscope cover and said endoscope cover attaching apparatus, according to claim 30, wherein said cover holding stage is in a substantially horizontal position in said initial state.

32. The combination of said endoscope, said endoscope cover and said endoscope cover attaching apparatus, according to claim 30, wherein said operation part is moved up and down.

33. The combination of said endoscope, said endoscope cover and said endoscope cover attaching apparatus, according to claim 30, wherein said operation part holding stage for holding said operation part is moved up and down by a hydraulic cylinder.

34. The combination of said endoscope, said endoscope cover and said endoscope cover attaching apparatus, according to claim 19 or 30, wherein said operation part holding stage is provided with a hanger for holding said operation part of said endoscope, and a hanger for holding an inlet portion of said endoscope cover.

35. The combination of said endoscope, said endoscope cover and said endoscope cover attaching apparatus, according to claim 34, wherein when said operation part of said endoscope is held by said hanger for holding said operation part of said endoscope, a universal cord extends from a side face of said operation part toward a control panel of an endoscope system placed on a cart.

36. The combination of said endoscope, said endoscope cover and said endoscope cover attaching apparatus, according to claim 34, wherein a height of said hanger for holding said operation part of said endoscope and a height of said hanger for holding said inlet portion of said endoscope cover are set to such values that a distance from a floor to an end face of said insertion part of said endoscope hung on a first hanger from a group made up of said hanger for holding said operation part of said endoscope and said hanger for holding said inlet portion of said endoscope cover is equal to a distance from a floor to an end face of said insertion part of said endoscope hung on a second hanger from said group made up of said hanger for holding said operation part of said endoscope and said hanger for holding said inlet portion of said endoscope cover.

37. The combination of said endoscope, said endoscope cover and said endoscope cover attaching apparatus, according to claim 25 or 30, wherein said operation part holding stage is provided with a stopper means for controlling a direction of rotation.

38. The combination of said endoscope, said endoscope cover and said endoscope cover attaching apparatus, according to claim 19, wherein said cover holding stage also serves as a package of said endoscope cover.

39. The combination of said endoscope, said endoscope cover and said endoscope cover attaching apparatus, according to claim 19, wherein a measure for indicating an attachment state of said endoscope to said endoscope cover is provided on said cover holding stage.

40. The combination of said endoscope, said endoscope cover and said endoscope cover attaching apparatus, according to claim 19, wherein a variable guide is provided on said cover holding stage, said variable guide being adaptive to a change in a diameter of said endoscope cover.

41. The combination of said endoscope, said endoscope cover and said endoscope cover attaching apparatus, according to claim 1 or 19, wherein a part of said cover holding stage on which an end portion of said endoscope cover is to be placed has a width greater than a width of said endoscope cover.

42. The combination of said endoscope, said endoscope cover and said endoscope cover attaching apparatus, according to claim 1 or 19, wherein an attachment operation can be performed to keep said endoscope cover covered with an over-tube.

* * * * *